United States Patent [19]

Van Daele et al.

[11] Patent Number: 4,968,684

[45] Date of Patent: Nov. 6, 1990

[54] METHOD OF IMPROVING SLEEP

[75] Inventors: Georges H. P. Van Daele, Turnhout; Freddy F. Vlaeminck, Lille; Marc G. C. Verdonck, Turnhout, all of Belgium

[73] Assignee: Janssen Pharmaceutica N.V., Beerse, Belgium

[21] Appl. No.: 419,349

[22] Filed: Oct. 10, 1989

Related U.S. Application Data

[63] Continuation of Ser. No. 165,965, Mar. 9, 1988, Pat. No. 4,880,808, which is a continuation-in-part of Ser. No. 34,129, Apr. 1, 1987, abandoned.

[51] Int. Cl.$^5$ .................. A61K 31/496; C07D 295/10; C07D 241/04
[52] U.S. Cl. .................. 514/255; 514/252; 544/360; 544/364; 544/390; 544/391; 544/396; 544/397
[58] Field of Search ............... 544/360, 390, 397, 400, 544/364, 391, 396; 514/252, 255

[56] References Cited

U.S. PATENT DOCUMENTS 4,766,125 8/1988 Van Daele .................. 514/255

Primary Examiner—Cecilia Shen
Attorney, Agent, or Firm—Charles J. Metz

[57] ABSTRACT

A method of improving sleep in warm-blooded animals suffering from sleep disorders, which method comprises the administration of particular N-aryl-piperazinealkanamide derivatives and compositions containing the same. Novel N-aryl-piperazinealkanamide derivatives.

16 Claims, No Drawings 4,968,684

1

METHOD OF IMPROVING SLEEP

CROSS-REFERENCE TO RELATED APPLICATIONS

This is a continuation of application Ser. No. 165,965, filed Mar. 9, 1988, now U.S. Pat. No. 4,880,808, which is a continuation-in-part of application Ser. No. 34,129 filed Apr. 1, 1987, now abandoned.

BACKGROUND OF THE INVENTION

A new method of treating sleep disorders is generally considered an important goal to achieve. Up until now, quite a number of preparations are known which effect sleep, said preparations containing usually as active ingredient hypnotics such as, benzodiazepines, barbiturates and the like.

The present invention provides a novel method of improving sleep and treating sleep disorders by applying particular N-aryl-piperazinealkanamide derivatives.

Some of the N-aryl-piperazinealkanamide derivatives of the present invention are known from the Eur. Pat. No. 0,068,644, and were taught to be useful for protecting the heart from myocardial injury caused by ischaemia, anoxia or hypoxia.

Further some N-aryl-piperazinealkanamide derivatives bearing an alkyl substituent on the piperazine moiety are described in U.S. Pat. No. 3,267,104 as coronary vasodilators, as local anaesthetics, as central nervous system stimulating agents, and as anticarrageenin agents.

However, most of the said N-aryl-piperazinealkanamide derivatives are novel and have especially been developed to be used as active substances in the method of the present invention.

DESCRIPTION OF THE INVENTION

The present invention is concerned with a method of improving sleep in warm-blooded animals suffering from sleep disorders, which method comprises the administration of an amount effective in improving sleep of a piperazine derivative having the formula:

$$Q-Alk-N\underset{R^1}{\overset{X}{\diagup\diagdown}}N-C_mH_{2m}-\overset{O}{\overset{\|}{C}}-\underset{R^2}{N}-Ar, \quad (I)$$

the stereochemically isomeric forms and the pharmaceutically acceptable acid addition salts thereof, wherein:

$R^1$ is hydrogen or $C_{1-6}$alkyl;

X is $C_{1-6}$alkyl, hydroxy$C_{1-6}$alkyl. $C_{1-6}$alkyloxy$C_{1-6}$alkyl, aminocarbonyl, mono- and di($C_{1-6}$)aminocarbonyl, carboxyl, $C_{1-6}$alkyloxycarbonyl, (aminocarbonyl)$C_{1-6}$alkyl, [mono- and di($C_{1-6}$alkyl)aminocarbonyl]$C_{1-6}$alkyl, carboxyl$C_{1-6}$alkyl, ($C_{1-6}$alkyloxycarbonyl)$C_{1-6}$alkyl or (hydroxy$C_{1-6}$alkyl)aminocarbonyl;

m is the integer 1 or 2;

$R^2$ is hydrogen or $C_{1-6}$alkyl;

Ar is phenyl, optionally substituted with up to 3 substituents each independently selected from the group consisting of hydroxy, $C_{1-6}$alkyl, $C_{1-6}$alkyloxy, halo, trifluoromethyl, $C_{1-6}$alkylcarbonyl,

2 mono- and di($C_{1-6}$alkyl)aminocarbonyl, aminocarbonyl, $C_{1-6}$alkyloxycarbonyl, nitro, cyano, amino, amino-methyl, mono- and di($C_{1-6}$alkyl)amino, ($C_{1-6}$alkylcarbonyl)amino, (aminocarbonyl)amino and phenylmethoxy; pyridinyl, optionally substituted with up to three substituents independently selected from halo and $C_{1-6}$alkyl; pyrazolyl, optionally substituted with up to three substituents independently selected from halo and $C_{1-6}$alkyl; or a radical of formula $$\underset{(CH_2)_s}{\overset{R^3\quad R^4}{\diagup\diagdown}}N \quad (a)$$

wherein $R^3$ and $R^4$ are each independently selected from the group consisting of halo, $C_{1-6}$alkyl, hydroxy and $C_{1-6}$alkyloxy and s is the integer 3, 4 or 5;

Alk is a $C_{1-6}$alkanediyl radical or a $C_{3-6}$alkenediyl radical, said $C_{1-6}$alkanediyl radical being optionally substituted with a hydroxy- or a $C_{1-6}$alkyl radical; and Q is aryl, aryloxy, diarylmethoxy, 2,2-diarylethenyl, diarylmethylcarbonyl, arylcarbonyl, mono- and diarylaminocarbonyl, diarylmethyl or arylamino, the amino moiety in said arylamino being optionally substituted with an aryl-, an arylcarbonyl-, a $C_{1-6}$alkylcarbonyl-, an arylsulfonyl- or a $C_{1-6}$alkylsulfonyl-radical; wherein aryl is phenyl, substituted phenyl, naphthalenyl, thienyl or pyridinyl, said substituted phenyl having from 1 to 2 substituents, each independently selected from the group consisting of halo and $C_{1-6}$alkyloxy.

In the foregoing definitions the term halo is generic to fluoro, chloro, bromo and iodo, with fluoro being preferred;

the term is meant to include straight and branched saturated hydrocarbon radicals having from 1 to 6 carbon atoms such as, for example, methyl, ethyl, 1-methylethyl, 1,1'-dimethylethyl, propyl, butyl, pentyl and the like:

"$C_{1-6}$alkanediyl" is meant to include bivalent straight or branch chained alkanediyl radicals having from 1 to 6 carbon atoms; and "$C_{3-6}$ alkenediyl" is meant to include bivalent straight and branch chained hydrocarbon radicals containing one double bond and having from 3 to 6 carbon atoms and when a $C_{3-6}$alkenediyl is substituted on a heteroatom, then the carbon atom of said $C_{3-6}$alkenediyl connected to said heteroatom preferably is saturated.

It is to be understood that the compounds of formula (I) may exist in hydrated or in solvent addition forms and that the invention includes all such forms.

Preferred compounds of formula (I) to be used in the method of the present invention are those compounds of formula (I) wherein $R^1$ and $R^2$ are both hydrogen; m is 1; and X is $C_{1-6}$alkyl, hydroxy$C_{1-6}$alkyl, aminocarbonyl or mono- and di($C_{1-6}$alkyl)aminocarbonyl.

Particularly preferred compounds to be used in the method of the present invention are those preferred compounds of formula (I) wherein Q is diarylmethoxy, 2,2-diarylethenyl, diarylaminocarbonyl, diarylmethyl or arylamino, the amino moiety in said arylamino being substituted with an aryl- or an arylcarbonyl radical; and said aryl being phenyl or substituted phenyl.

Especially preferred compounds to be used in the method of the invention are those particularly preferred compounds of formula (I) wherein Q-Alk- is 5,5-di(-halophenyl)pentenyl or 5,5-di(halophenyl)pentyl.

An interesting subgroup of compounds of formula (I) to be used in the present invention comprises those compounds, preferred or particularly preferred compounds wherein Alk is $C_{3-5}$alkanediyl, with those compounds having five atoms between the piperazine moiety and the aryl or diaryl moiety in Q constituting a particularly interesting subgroup.

Most preferred compounds to be used in the method of the invention are selected from the group consisting of 2-(aminocarbonyl)-N-(4-amino-2,6-dichlorophenyl)-4-[5,5-bis(4-fluorophenyl)pentyl]-1-piperazineacetamide, the pharmaceutically acceptable acid addition salts and the possible stereochemically isomeric forms thereof.

Some compounds of formula (I) used in the method of the present invention are known from U.S. Pat. No. 3,267,104 and from the Eur. Pat. No. 0,068,544 which corresponds to U.S. Ser. No. 362,814, while others are new. The preparation of the compounds of formula (I), both novel ones and known ones, will be described hereinafter in more detail.

The compounds of formula (I) can generally be prepared by N-alkylating an appropriately substituted piperazine of formula (II) with a reagent of formula (III) or by N-alkylating an appropriately substituted piperazine of formula (IV) with a reagent of formula (V).

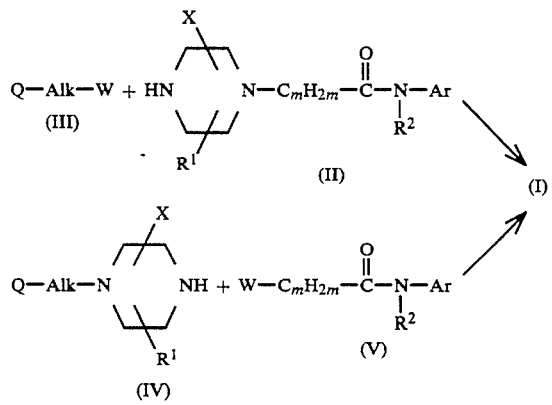

In the above reaction scheme Q, Alk, $R^1$, $R^2$, X, Ar and m are as previously described and W represents an appropriate leaving group such as, for example, halo, e.g., chloro, bromo or iodo, or a sulfonyloxy group, e.g., methylsulfonyloxy or 4-methylphenylsulfonyloxy.

The N-alkylation reaction of (II) with (III) and (IV) with (V) is conveniently conducted in an inert organic solvent such as, for example, an aromatic hydrocarbon, e.g., benzene, methylbenzene, dimethylbenzene, and the like; a lower alkanol, e.g., methanol, ethanol, 1-butanol and the like; a ketone, e.g., 2-propanone. 4-methyl-2-pentanone and the like; an ether, e.g., 1,4-dioxane, 1,1'-oxybisethane, tetrahydrofuran, methoxyethanol and the like; a polar aprotic solvent, e.g., N,N-dimethylformamide (DMF), N,N-dimethylacetamide (DMA), nitrobenzene, dimethyl sulfoxide (DMSO), 1-methyl-2-pyrrolidinone, and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be appropriate to pick up the acid which is liberated during the course of the reaction. In some instances the addition of a iodide salt, preferably an alkali metal iodide, is appropriate. Somewhat elevated temperatures may enhance the rate of the reaction. The compounds of formula (1) may also be prepared by reacting a piperazine of formula (II) with the corresponding carbonyl-oxidated form of the reagent of formula (III), following art-known reductive amination procedures, i.e. by stirring and, if desired heating the reactants in a suitable reductive medium, e.g., under catalytic hydrogenation procedures. The compounds of formula (I) may also be prepared by the reaction of carboxylic acid derivative of formula (VI), wherein $R^5$ is hydroxy, $C_{1-6}$alkyloxy, aryloxy, amino, chloro, $C_{1-6}$alkyloxycarbonyloxy, or a sulfonyloxy group, with an amine of formula (VII) by stirring and, if desired, heating the reactants together in a suitable solvent such as, for example, an alkanol, e.g., methanol or ethanol; an ether, e.g., 1,4-dioxane or tetrahydrofuran; N,N-dimethylformamide or 4-methyl-2-pentanone.

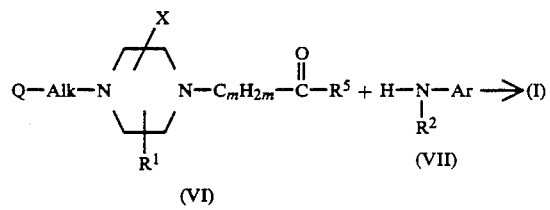

In some instances the compounds of formula (I) may also be prepared following alternative procedures described in Eur. Pat. No. 0.068,544 which are incorporated herein as a reference.

The compounds of formula (I) can also be converted into each other following art-known procedures of functional group transformation. Some examples of such procedures will be cited hereinafter.

(a) The compounds of formula (I) wherein X is a carboxyl function may be converted into the corresponding compounds of formula (I) wherein X is an ester function or an amide function following art-known procedures, e.g., by stirring and, if desired, heating the starting carboxylic acid with an appropriate alcohol, respectively, an appropriate amine. The said compounds wherein X is a carboxylic acid function may also be converted into the corresponding esters by reacting the starting compounds of formula (I) wherein X is a carboxyl function with an appropriate alkyl halide in the presence of a base, e.g., sodium methoxide and the like.

(b) The compounds of formula (I) wherein Ar is other than phenyl substituted with $C_{1-6}$alkyloxycarbonyl. aminocarbonyl or mono- or di($C_{1-6}$alkyl)aminocarbonyl, and wherein X is $C_{1-6}$alkylcarbonyl, aminocarbonyl or mono- or di($C_{1-6}$alkyl)aminocarbonyl may be converted into the corresponding compounds of formula (I) wherein X is a carboxylic acid function by stirring and, if desired, heating the starting compound into acidic- or alkaline aqueous medium.

(c) The compounds of formula (I) wherein Ar is other than phenyl substituted with a $C_{1-6}$alkyloxycarbonyl, and wherein X is a $C_{1-6}$alkyloxycarbonyl group may be converted into the corresponding compounds of formula (I) wherein X is an amide function by stirring and, if desired, heating the starting compound in the presence of an appropriate amine in a suitable reaction-inert solvent.

(d) The compounds of formula (I) wherein Ar is other than phenyl substituted with aminocarbonyl or $C_{1-6}$alkylaminocarbonyl and wherein X is aminocarbonyl or $C_{1-6}$alkylaminocarbonyl may be converted into compounds of formula (I) wherein X is a mono-, respectively a di($C_{1-6}$alkyl)aminocarbonyl; by stirring and, if desired, heating the starting compound with an appropriate $C_{1-6}$alkyl halide following art-known N-alkylating procedures.

(e) The compounds of formula (I) wherein Ar is other than phenyl substituted with carboxyl or $C_{1-6}$alkyloxycarbonyl and wherein X is carbonyl or lower $C_{1-6}$alkyloxyoarbonyl may be converted into the corresponding compounds of formula (I) wherein X is hydroxymethyl following art-known reduction procedures such as, for example, with metal hydrides, diborane and the like.

(f) The compounds of formula (I) wherein Ar is other than phenyl substituted with a hydroxy group and X is hydroxymethyl can be converted into the corresponding compounds of formula (I) wherein X is a carboxylic acid function following art-known alcohol-to-carboxylic acid oxidizing procedures, e.g., with potassium permanganate; chromic trioxide, silver oxide and the like.

(g) The compounds of formula (I) wherein X is a hydroxymethyl group can be converted into the corresponding compounds of formula (I) wherein X is a $C_{1-6}$alkyloxymethyl group following art-known procedures, e.g., by reacting the starting alcohol with an appropriate alkyl halide in the presence of a suitable base such as sodium hydride and the like in a suitable reaction inert solvent.

(h) The compounds of formula (I) wherein X is a $C_{1-6}$alkyloxymethyl group can be converted into the compounds of formula (I) wherein X is hydroxymethyl following art-known ether-cleavage procedures, e.g., by reacting the starting ether with a strong Lewis acid, such as, for example, boron trifluoride and the like.

(i) The compounds of formula (I) wherein Ar is phenyl substituted with nitro and Q is other than diarylmethylcarbonyl, mono- or diarylaminocarbonyl or arylamino, wherein said amino moiety is substituted with a $C_{1-6}$alkylcarbonyl radical, can be converted into the corresponding amines by stirring and, if desired, heating the starting nitro-compounds in a hydrogen-containing medium in the presence of a suitable amount of an appropriate catalyst such as, for example, platinum-on-charcoal, palladium-on-charcoal, Raney-nickel and the like catalyst. Suitable solvents are, for example methanol, ethanol and the like.

(j) Some compounds of formula (I) wherein Ar is phenyl substituted with one or more amino function(s) may further be derivatized following art-known procedures such as, for example, N-alkylation, N-acylation, reductive N-alkylation and the like procedures.

(1) $C_{1-6}$alkylcarbonyl groups may be introduced by reacting the starting amine with an appropriate carboxylic acid or a derivative thereof such as, for example, and acid halide, acid anhydride and the like in a suitable reaction-inert solvent;

(2) groups may be introduced by reacting the starting amine with an alkanal or alkanone under a hydrogen atmosphere and in the presence of an appropriate catalyst such as, palladium-on-charcoal, platinum-on-charcoal and the like catalysts in suitable solvent such as, methanol, ethanol and the like. In order to prevent the undesired further hydrogenation of certain functional groups in the reactants and the reaction products it may be advantageous to add an appropriate catalyst-poison to the reaction mixture, e.g., thiophene and the like;

(3) an aminocarbonyl group may be introduced by reacting the starting amine with an appropriate alkali metal cyanate in an acidic aqueous solution.

(h) Some compounds of formula (I) wherein Ar is phenyl substituted with phenylmethoxy may be converted into compounds of formula (I) wherein Ar is phenyl substituted with hydroxy following art-known catalytic hydrogenolysis procedures.

(l) some compounds of formula (I) wherein Ar is phenyl substituted with cyano group may partially by hydrolysed thus yielding the corresponding compounds wherein phenyl is substituted with an aminocarbonyl group. The hydrolysis reaction is preferably conducted in an aqueous acidic medium, e.g., an aqueous sulfuric, hydrochloric or phosphoric acid solution, at room temperature or at a slightly increased temperature.

(m) Some compounds of formula (I) wherein Ar is phenyl substituted with a cyano group may also be converted in the corresponding aminomethylphenyl compounds by stirring the starting cyanide compounds in a hydrogen-containing medium in the presence of a suitable amount of an appropriate catalyst such as, for example, palladium-on-charcoal in an appropriate solvent such as methanol.

In all the foregoing and in the following preparations, the reaction products may be isolated from the reaction mixture and, if necessary, further purified according to methodologies generally known in the art.

The compounds of formula (I) can be used as such or in their acid-addition salt form. The latter can conveniently be obtained by treating the base-form with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

Some of the intermediates and starting materials in the foregoing preparations are known compounds while others are novel. They may be prepared according to art-known methodologies of preparing said known or similarly known compounds. Some procedures for preparing such intermediates will be described hereinafter in more detail.

The intermediates of formula (IV) and (II) can be derived from an appropriately substituted piperazine of formula (VIII), by reacting the latter with a reagent of formula (III) and (V) respectively, following N-alkylation procedures described for the preparation of (I) starting from (II) and (III) and, subsequently, removing the protective group P in the thus obtained intermediates (IV-a) and (II-a).

difference in reactivity of both nitrogen atoms allows a specific N-alkylation due to the nature of the substituents X and $R^1$.

The piperazine of formula (VIII), used as a starting material, can be prepared following the same procedures as those described in the Eur. Pat. Publ. No. 0.068,544 and in U.S. Pat. No. 3,267,104 both incorporated herein as a reference.

The intermediates of formula (II) and (IV) bearing a radical of formula $—C(=O)—NHR^6$ said $R^6$ being hy-

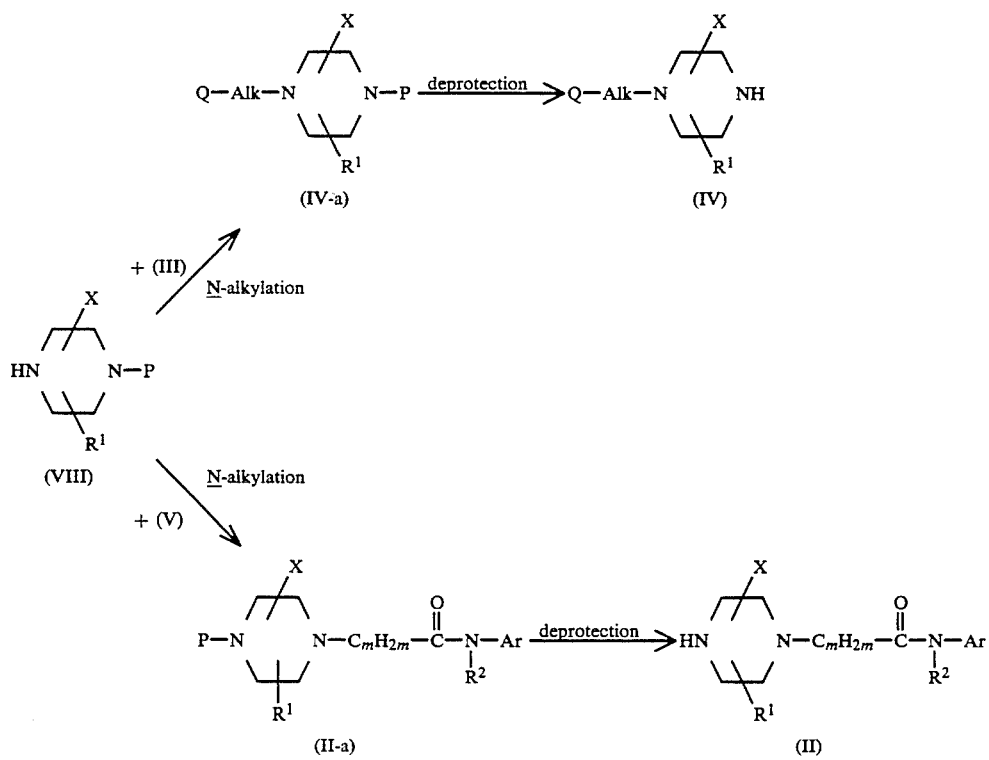

In formulae (VIII), (IV-a) and (II-a), P represents a protective group which is readily removable by hydrogenation or hydrolysation, such as, for example, phenylmethyl, $C_{1-4}$alkyloxycarbonyl e.g., ethoxycarbonyl, 1,1'-dimethylethyloxycarbonyl, and the like groups.

In some instances, the intermediates (IV) and (II) may also be prepared from an unprotected analogue of formula (VI) wherein P is hydrogen. Particularly when the drogen or $C_{1-6}$alkyl, in the α-position of the secondary amine function, (II-b) and (IV-b), may also be prepared by reacting an intermediate of formula (IX) with a reagent of formula (V) and (III) respectively, following the N-alkylation procedures described for the preparation of (I) starting from (II) and (III) and, subsequently hydrolyzing the thus obtained (X) and (XI) in an appropriate medium, preferably, an acidic aqueous medium.

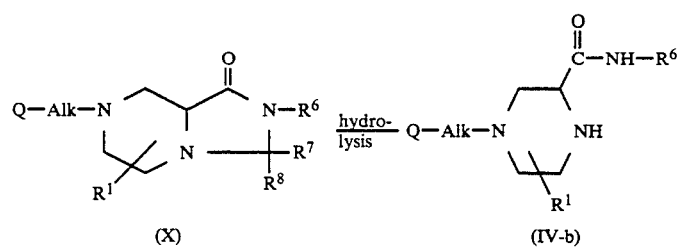

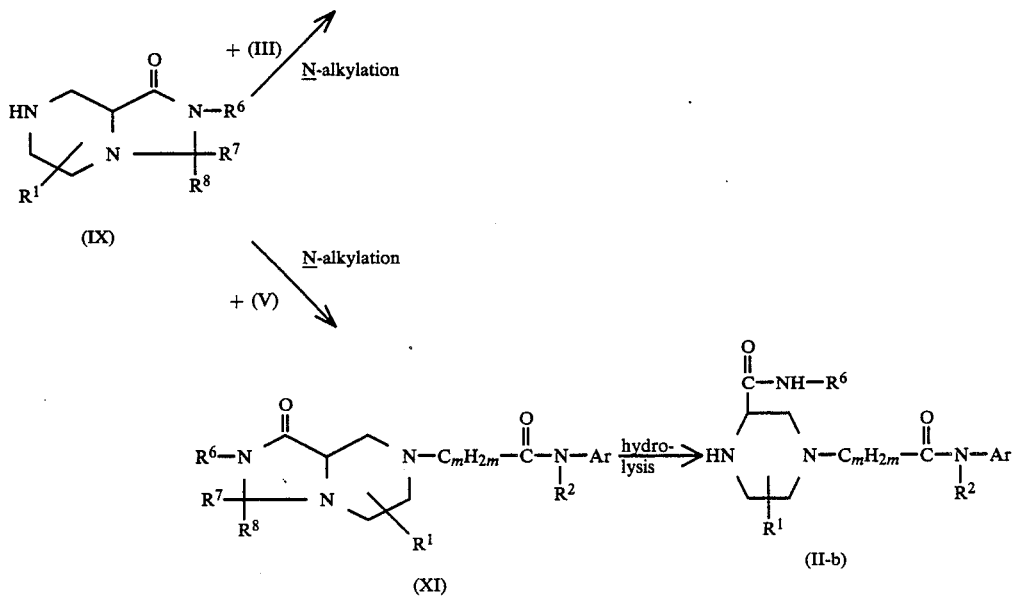

In the foregoing reaction scheme $R^7$ and $R^8$ each independently represents hydrogen of $C_{1-6}$alkyl.

The intermediates of formula (V) can be prepared by reacting an appropriate acid halide (XII) with an amine (VII) optionally in a suitable solvent, such as an aromatic hydrocarbon and the like.

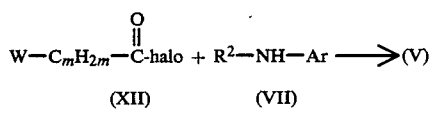

(XII)      (VII)

In the foregoing reaction schemes W has the same meaning as described hereinabove.

The starting amines of formula (VII) wherein Ar is a radical of formula (a) can be prepared following procedures described in, for example, the Journal of the American Chemical Society 71, 2205 (1949) and the Journal of the Pharmaceutical Society of Japan 72, 665 (1952), those starting amines of formula (VII) wherein Ar is a substituted pyridinyl can be prepared following procedures described in, for example, Chemische Berichte, 72, 577–581 (1939).

The intermediates of formula (III) may be prepared following art-known procedures, as described, in for example, the Eur. Pat. No. 0,068,544. More particularly, the following preparation procedures may be mentioned. Intermediates of formula (III) wherein Q is 2,2-diarylethenyl may be prepared by addition of an appropriate wittig reagent $(C_6H_5)_3P^+$-Alk'-COOH.Br$^-$ (XIII) on a diarylmethanone following procedures described in Eur. Pat. Publ. No. 0,098,690. The carboxylic acid moiety in the thus obtained diarylalkenoic acid may subsequently be reduced and converted into an appropriate leaving group following art-known procedures. Alk' in formula (XIII) being the same as Alk provided that a methylene group is missing.

Intermediates of formula (III) wherein Q is diarylmethoxy may be obtained by reducing a diarylmethanone with an appropriate reductant, such as, for example, sodium borohydride, and O-alkylating the thus obtained diarylmethanol with an appropriate dihaloalkane.

Or, intermediates of formula (III) wherein Q is diaryl aminocarbonyl can be prepared by reacting a diarylamine with an appropriate haloalkanoyl chloride. The thus obtained intermediate of formula (III) wherein Q is diarylaminocarbonyl may further be converted into the corresponding compounds wherein Q is diarylaminomethyl by reducing the amide moiety with an appropriate reductant such as, for example, a boranemethyl sulfide complex in a suitable solvent e.g., tetrahydrofuran.

The compounds of formula (I) and some of the intermediates in this invention have one or more asymmetric carbon atoms in their structure. Each of these chiral centers may be present in a R- and a S-configuration, this R- and S-notation being in correspondence with the rules described by R. S. Cahn, C. Ingold and V. Prelog in Angew. Chem., Int. Ed. Engl., 5, 385, 511 (1966).

The compounds of formula (I) containing an alkene moiety may be present in a "E" or "Z" form, said E- and Z- notation having the meanings described in J. Org. Chem., 35, 2849–2868 (1970).

Pure stereochemically isomeric forms of the compounds of formula (I) may be obtained by the application of art-known procedures. Diastereoisomers may be separated by physical separation methods such as selective crystallization and chromatographic techniques, e.g., counter current distribution, and enantiomers may be separated from each other by the selective crystallization of their diastereomeric salts with optically active acids.

Pure stereochemically isomeric forms may also be derived from the corresponding pure stereochemically isomeric forms of the appropriate starting materials, provided that the reaction occurs stereospecifically.

It is evident that the cis and trans diastereomeric racemates may be further resolved into their optical isomers, cis(+), cis(−), trans(+) and trans(−) by the application of methodologies known to those skilled in the art.

As mentioned hereinabove a number of the active ingredients of formula (I) are novel and have especially been developed to be used as active substances in the method of the present invention. These compounds constituting a further aspect of the present invention can be represented by the formula

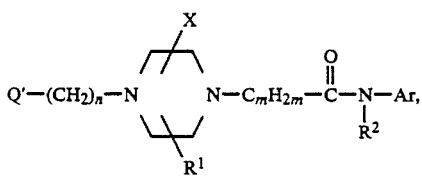

the pharmaceutically acceptable acid addition salts and the stereochemically isomeric forms thereof, wherein $R^1$, $R^2$, X, m and Ar have the previously described meanings; $-(CH_2)_n-$ is a bivalent radical wherein n is an integer from 1 to 4 when Ar is other than phenyl or substituted phenyl, or n is the integer 3 or 4 when Ar is phenyl or substituted phenyl, and wherein one hydrogen in said bivalent radical may be replaced by $C_{1-6}$alkyl; and Q' is arylethyl, arylethenyl, aryloxymethyl, diarylmethoxy, 2,2-diarylethenyl, diarylmethylcarbonyl, arylcarbonylmethyl, mono- and diarylaminocarbonyl, diarylethyl or arylaminomethyl, the amino moiety in said arylaminomethyl being optionally substituted with an aryl-, an arylcarbonyl-, a $C_{1-6}$alkylcarbonyl-, an arylsulfonyl- or a $C_{1-6}$alkylsulfonyl radical; provided that Q' is other than 2,2-di(-halophenyl)ethyl when Ar is dihalophenyl and X is aminocarbonyl.

Preferred novel compounds are those compounds of formula (I') wherein $R^1$ and $R^2$ are both hydrogen; m is 1; and X is $C_{1-6}$alkyl, hydroxy$C_{1-6}$alkyl, aminocarbonyl or mono- and di($C_{1-6}$alkyl)aminocarbonyl.

Particularly preferred novel compounds are those preferred novel compounds wherein Q' is diarylmethoxy, 2,2-diarylethenyl, diarylaminocarbonyl, 2,2-diarylethyl or arylaminomethyl, the amino moiety in said arylaminomethyl being substituted with an aryl- or an arylcarbonyl radical; and wherein said aryl is phenyl or substituted phenyl.

Especially preferred novel compounds are those particularly preferred novel compounds wherein Q' is 2,2-dihalophenylethenyl or 2,2-dihalophenylethyl.

An interesting subgroup of novel compounds of formula (I') comprises those compounds, preferred, particularly preferred or especially preferred novel compounds wherein Ar is optionally substituted pyridinyl, optionally substituted pyrazolyl or a radical of formula (a).

Another interesting subgroup of novel compounds of formula (I') comprises those compounds, preferred, particularly preferred or especially preferred novel compounds wherein Ar is phenyl or substituted phenyl, n is 3 and X is $C_{1-4}$alkyl.

Still another interesting subgroup of novel compounds of formula (I') comprises those compounds, preferred, particularly preferred or especially preferred novel compounds wherein Ar is 2,6-dihalophenyl substituted in the 4-position with amino, mono- and di($C_{1-4}$alkyl)amino, $C_{1-4}$alkylcarbonylamino, aminocarbonylamino, $C_{1-4}$alkylcarbonyl, aminocarbonyl, cyano or halo.

The use of the compounds of formula (I), the pharmaceutically acceptable acid-addition salts and stereochemically isomeric forms thereof in the method of the present invention is based on their useful sleep improving properties. More particularly, they increase the total sleep, primarily through enhancement of slow wave sleep and decrease of wakening. This property is clearly evidenced by the results obtained in the "Slow-wave Sleep in Dogs"-test. By virtue of their ability to improve sleep it is evident that the compounds of the present invention are useful for improving sleep in warm-blooded animals suffering from sleep disorders.

An additional advantage of the method of the present invention comprises the fact that the compounds of formula (I) show the aforementioned sleep improving properties upon oral administration. Apart from their sleep-improving properties, the compounds of the present invention and more particularly the novel compounds of formula (I') also possess the same useful pharmacological properties of the compounds of the Publ. Eur. Pat. appl. No. 68,644 and more particularly of the preferred compound thereof, i.e., 3-(aminocarbonyl)-4-[4,4-bis(4-fluorophenyl)butyl]-N-(2,6-dichlorophenyl)-1-piperazineacetamide which generically is designated as mioflazine. Said useful pharmacological properties are described in the mentioned publ. Eur. Pat. Appl. No. 68,644 and e.g. in Cardiovascular Research, 18, 528–537 (1984), in Cardiovascular Research, 20, 658–664 (1986), and more particularly comprise the capability to ameliorate the blood perfusion of the muscular tissues of the heart, the protection of the heart from myocardial injury, the protection against myocardial calcium-over-load and the inhibition of nucleoside transport.

The compounds used in the method of the present invention are most preferably applied in form of appropriate compositions.

To prepare the pharmaceutical compositions of this invention, an effective amount of the compound of formula (I), in base or acid-addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoon-fuls and the like, and segregated multiples thereof.

Those of skill in the pertinent art could easily determine the effective sleep-improving amount from the results presented hereinafter. In general it is contemplated that an effective amount would be from 0.001 mg/kg to 100 mg/kg body weight, and more preferably from 0.01 mg/kg to 10 mg/kg body weight.

The following examples are intended to illustrate and not to limit the scope of the invention.

Unless otherwise stated all parts therein are by weight.

EXPERIMENTAL PART

A. Preparation of intermediates

Example 1

(a) A mixture of 13.36 parts of 2-chloro-N-[2,6-dimethyl-4-(phenylmethoxy)phenyl]acetamide, 6.76 parts of hexahydro-3.3-dimethylimidazo[1,5-a]pyrazin-1(5H)-one, 7.8 parts of N,N-diethylethanamine and 180 parts of N,N-dimethylformamide was stirred for 20 hours at 70° C. The reaction mixture was evaporated. The residue was taken up in water and the product was extracted twice with dichloromethane. The combined extracts were washed with water, dried, filtered and evaporated. The residue was purified by column chromatography over silica gel using a mixture of trichloromethane and methanol (95:5 by volume) as eluent. The desired fraction was collected and the eluent was evaporated. The residue was crystallized from acetonitrile. The product was filtered off and dried, yielding 11.66 parts (66.8%) of N-[2,6-dimethyl-4-(phenylmethoxy)-phenyl]hexahydro-3,3-dimethyl-1-oxoimidazo-[1,5-a]pyrazine-7(8H)-acetamide; mp. 223.8° C. (int. 1).

(b) A mixture of 11.10 parts of N-[2,6-dimethyl-4-(phenylmethoxy)phenyl]hexahydro-3,3-dimethyl-1-oxoimidazo[1,5-a]pyrazine-7(8H)acetamide and 100 parts of a hydrochloric acid solution 0.5N was stirred for 2 hours at reflux temperature. After cooling, the reaction mixture was treated with a sodium hydroxide solution 50%. The product was extracted twice with dichloromethane. The combined extracts were dried, filtered and evaporated. The residue was suspended in 2,2'-oxybispropane. The product was filtered off and dried, yielding 8.19 parts (82.6%) of 3-(aminocarbonyl)-N-[2,6-dimethyl-4-(phenylmethoxy)phenyl]-1-piperazineacetamide (int. 2).

In a similar manner there were also prepared:
3-(aminocarbonyl)-N-(5-fluoro-2-methylphenyl)-1-piperazineacetamide; mp. 168.6° C. (int. 3);
3-(aminocarbonyl)-N-(2-chloro-6-methylphenyl)-1-piperazineacetamide; mp. 176.6° C. (int. 4);
3-(aminocarbonyl)-N-(2,6-dichloro-4-cyanophenyl)-1-piperazineacetamide; mp. 205.5° C. (int. 5);
N-(4-acetyl-2,6-dichlorophenyl)-3-(aminocarbonyl)-1-piperazineacetamide (int. 6);
3-(aminocarbonyl)-N-(2,4,6-trichlorophenyl)-1-piperazineacetamide (int. 7);
3-(aminocarbonyl)-N-(4-(aminocarbonyl)-2,6-dichlorophenyl)-1-piperazineacetamide; mp. 256.8° C. (int. 8);
3-(aminocarbonyl)-N-(2,6-diethylphenyl)-1-piperazineacetamide; mp. 166.9° C. (int. 9):
N-(3-acetyl-2,6-dimethylphenyl)-3-(aminocarbonyl)-1-piperazineacetamide (int. 10);
N-(3-acetyl-2,6-dimethylphenyl)-3-[(methylamino)carbonyl]-1-piperazineacetamide (int. 11) and
N-(2,6-diethylphenyl)-3-(methylaminocarbonyl)-1-piperazineacetamide: mp. 138.1° C. (int. 12).

Example 2

A mixture of 15.33 parts of N-methyl-2-piperazinecarboxamide, 27.2 parts of 2-chloro-N-(2,4,6-trichlorophenyl)acetamide, 9.8 parts of N,N-diethylethanamine and 300 parts of 2-methoxyethanol was stirred for 3 hours at 60° C. The reaction mixture was evaporated. The residue was taken up in a small amount of water and treated with sodium carbonate. The product was extracted three times with dichloromethane. The combined extracts were dried, filtered and evaporated. The residue was crystallized from acetonitrile. The product was filtered off (the filtrate was set aside) and dried, yielding a first fraction of 9.27 parts (24.4%) of 3-((methylamino)carbonyl)-N-(2,4,6-trichlorophenyl)-1-piperazineacetamide.

The filtrate, which was set aside (see above) was evaporated. The residue was purified by column chromatography over silica gel using a mixture of trichloromethane and 2-propanol (90:10 by volume) as eluent. The desired fraction was collected and the eluent was evaporated. The residue was crystallized from acetonitrile. The product was filtered off and dried, yielding a second fraction of 5.93 parts (15.6%) of 3-[(methylamino)carbonyl]-N-(2,4,6-trichlorophenyl)-1-piperazineacetamide: mp. 168.9° C.

Total yield: 15.2 parts (40.0%) of 3-[(methylamino)carbonyl]-N-(2,4,6-trichlorophenyl)-1-piperazineacetamide (int. 13).

In a similar manner there were also prepared:
N-(2,6-dimethylphenyl)-3-(hydroxymethyl)-1-piperazineacetamide; mp. 135.1° C. (int. 14);
N-(2-acetylphenyl)-3-(aminocarbonyl)-1-piperazineacetamide (int. 15);
N-(4-acetyl-2,6-dichlorophenyl)-3-[(methylamino)carbonyl]-1-piperazineacetamide (int. 16);
N-(3-chloro-2,5,6,7-tetrahydro-2-oxo-1H-1-pyrindin-4-yl)-3-(methylaminocarbonyl)-1-piperazineacetamide (int. 17);
3-[(methylamino)carbonyl]-N-(2,4,6-trimethyl-3-pyridinyl)-1-piperazineacetamide as a residue (int. 18) and
N-(4-acetyl-2,6-dichlorophenyl)-3-methyl-1-piperazineacetamide as a residue (int. 19).

Example 3

(a) To a stirred solution of 60 parts of 2-methylpiperazine in 1500 parts of trichloromethane was added dropwise a solution of 46 parts of bis(1,1'-dimethylethyl)dicarbonate in 75 parts of trichloromethane at 10°-15° C. during 90 minutes. Upon complete addition, stirring was continued for 1 hour at room temperature. The reaction mixture was washed twice with water, dried, filtered and evaporated, yielding 52 parts (100%) of (1,1-dimethylethyl) 3-methyl-1-piperazinecarboxylate as a residue (int. 20).

(b) A mixture of 12 parts of (1,1-dimethylethyl) 3-methyl-1-piperazinecarboxylate, 18.7 parts of N-(4-acetyl-2,6-dichlorophenyl)-2-chloroacetamide, 11.8 parts of N,N-diethylethanamine and 230 parts of N,N-dimethylformamide was stirred first for 8 hours at 70° C. and then over weekend at room temperature. The reaction mixture was evaporated and the residue was taken up in water. The product was extracted twice with dichloromethane. The combined extracts were washed with water, dried, filtered and evaporated. The residue was purified by column chromatography over silica gel using trichloromethane as eluent. The desired fraction was collected and the eluent was evaporated, yielding 27 parts (100%) of (1,1-dimethylethyl) 4-[2-[(4-acetyl-2,6-dichlorophenyl)amino]-2-oxoethyl]-3-methyl-1-piperazinecarboxylate as a residue (int. 21).

(c) Gaseous hydrogen chloride was bubbled through a mixture of 87 parts of (1,1-dimethylethyl) 4-[2-[(4-acetyl-2,6-dichlorophenyl)amino)-2oxoethyl]-3-methyl-1-piperazinecarboxylate and 40% parts of methanol. The whole was stirred for 15 minutes at reflux temperature. The reaction mixture was evaporated and the residue was taken up in water. The whole was treated with an ammonium hydroxide solution and the product was extracted twice with dichloromethane. The combined extracts were dried, filtered and evaporated. The residue was suspended in 2,2'-oxybispropane. The product was filtered off and dried, yielding 15 parts (72.6%) of N-(4-acetyl-2,6-dichlorophenyl)-2-methyl-1-piperazineacetamide (int. 22).

In a similar manner there was also prepared:
N-(3-bromo-6,7-dihydro-5H-1-pyrindin-4-yl)-2-methyl-1-piperazineacetamide (int. 23).

Example 4

(a) A mixture of 51 parts of 1,1'-(5-bromo-1-penten-1-ylidene)bis[4-fluorobenzene], 25.4 parts of hexahydro-3,3-dimethylimidazo-[1,5-a]pyrazin-1(5H)-one, 35.5 parts of N,N-diethylethanamine and 270 parts of N,N-dimethylformamide was stirred overnight at 70° C. After evaporation, the residue was taken up in trichloromethane. The organic layer was washed with water, dried, filtered and evaporated. The residue was purified by column chromatography over silica gel using a mixture of trichloromethane and methanol (96:4 by volume) as eluent. The pure fractions were collected and the eluent was evaporated, yielding 60 parts (94.0%) of 7-[5,5-bis(4-fluorophenyl)-4-pentenyl]hexahydro-3,3-dimethylimidazo[1.5-a]pyrazin-1(5H)-one as a residue (int. 24).

(b) A mixture of 60 parts of 7-[5,5-bis(4-fluorophenyl)-4-pentenyl]hexahydro-3,3-dimethylimidazo[1,5-a]pyrazin-1(5H)-one and 850 parts of a hydrochloric acid solution 0.5N was stirred for 2 hours at reflux temperature. After cooling, the reaction mixture was treated with potassium carbonate. The product was extracted with trichloromethane. The extract was dried, filtered and evaporated. The residue was purified by column chromatography over silica gel using a mixture of trichloromethane and methanol (95:5 by volume) as eluent. The pure fractions were collected and the eluent was evaporated. The residue was crystallized from 1,1'-oxybisethane. The product was filtered off and dried, yielding 29.5 parts (50%) of 4-[5,5-bis(4-fluorophenyl)-4-pentenyl]-2-piperazinecarboxamide monohydrate; mp. 51.3° C. (int. 25).

In a similar manner there were also prepared:
4-(5,5-bis(4-fluorophenyl)pentyl)-2-piperazinecarboxamide (int. 26);
4-(5,5-diphenylpentyl)-2-piperazinecarboxamide (int. 27).

Example 5

A mixture of 17.7 parts of N-(4-chlorobutyl)-4-fluoro-N-(4-fluorophenyl)benzenamine. 23.3 parts of 2-piperazinecarboxamide, 17.6 parts of N,N-diethylethanamine and 300 parts of 2-methoxyethanol was stirred for 48 hours at 70° C. The reaction mixture was evaporated and the residue was taken up in water and a small amount of methanol. The product was extracted twice with dichloromethane. The combined extracts were washed with water, dried, filtered and evaporated. The residue was purified by column chromatography over silica gel using a mixture of trichloromethane and methanol, saturated with ammonia, (95:5 by volume) as eluent. The pure fraction was collected and the eluent was evaporated. The residue was crystallized from a mixture of 2,2'-oxybispropane and acetonitrile (80:20 by volume). The product was filtered off and dried, yielding 12.82 parts (55.0%) of 4-[4-[bis-(4-fluorophenyl)amino]butyl]-2-piperazinecarboxamide; mp. 67.4° C. (int. 28).

In a similar manner there was also prepared:
4-[3-[bis(4-fluorophenyl)methoxy]propyl]-2-piperazinecarboxamide as a residue (int. 29);
N,N-bis(4-fluorophenyl)-3-methyl-1-piperazinebutanamide as a residue (int. 30);
3-(aminocarbonyl)-N,N-bis(4-fluorophenyl)-1-piperazinebutanamide as a residue (int. 31) and
4-[5,5-bis(4-fluorophenyl)pentyl]-N-methyl-2-piperazinecarboxamide as a residue (int. 32).

Example 6

(a) A mixture of 74.2 parts of 1,1'-(5-bromo-1-penten-1-ylidene)bis[4-fluorobenzene], 43.8 parts of 4-(phenylmethyl)-2-piperazinecarboxamide, 38.9 parts of N,N-diethylethanamine and 1350 parts of N,N-dimethylformamide was stirred for 20 hours at 70° C. The reaction mixture was evaporated in vacuo and the residue was stirred in dichloromethane. The precipitate was filtered off. The filtrate was washed three times with 200 parts of water and once with 200 parts of a diluted ammonium hydroxide solution, dried, filtered and evaporated. The residue was purified by column chromatography over silica gel using a mixture of trichloromethane and methanol (97:3 by volume) as eluent. The pure fractions were collected and the eluent was evaporated, yielding 58.9 parts (61.9%) of 1-[5,5-bis(4-fluorophenyl)-4-pentenyl]-4-(phenylmethyl)-2-piperazinecarboxamide as a residue (int. 33).

(b) A solution of 56.9 parts of 1-[5,5-bis(4-fluorophenyl)-4-pentenyl]-4-(phenylmethyl)-2-piperazinecarboxamide in 400 parts of methanol was hydrogenated in a Parr apparatus and at 50° C. with 5 parts of palladium-on-charcoal catalyst 10%. After the calculated amount of hydrogen was taken up, the catalyst was filtered off and the filtrate was evaporated in vacuo. The residue was dissolved in 2-propanone and the whole was acidified with a mixture of hydrochloric acid and 2-propanol. After the addition of 2,2'-oxybispropane, the supernatant liquid was decanted and the precipitate was stirred in 2,2'-oxybispropane. The precipitated product was filtered off and dissolved in water. After washing with 2,2'-oxybispropane, the aqueous layer was treated with ammonium hydroxide and the product was extracted with trichloromethane. The extract was washed with a sodium chloride solution, dried, filtered and evaporated (under trichloromethane), yielding 35.2 parts (76.3%) of 1-[5,5-bis(4-fluorophenyl)pentyl]-2-piperazinecarboxamide as a residue (int. 34).

In a similar manner there was also prepared:
1-[5,5-bis(4-fluorophenyl)pentyl]-2-methylpiperazine as a residue (int. 35).

EXAMPLE 7

(a) 580 parts of a sodium hydroxide solution 1N in water were cooled in an ice bath and then there were added 44 parts of 3-methyl-1-(phenylmethyl)piperazine and 82.8 parts of tetrahydrofuran. A solution of 27.13 parts of ethyl carbonochloridate in 103.5 parts of tetrahydrofuran was added dropwise at a temperature at about 5° C. Upon completion, stirring was continued for 4 hours in an ice bath. The product was extracted with dichloromethane. The extract was washed with water, dried, filtered and evaporated. The residue was purified by column chromatography over silica gel using a mixture of trichloromethane and methanol (99:1 by volume) as eluent. The pure fractions were collected and the eluent was evaporated, yielding 55 parts (87.8%) of ethyl 2-methyl-4-(phenylmethyl)-1-piperazinecarboxylate as a residue (int. 36).

(b) A mixture of 21 parts of ethyl 2-methyl-4-(phenylmethyl)-1-piperazinecarboxylate and 200 parts of methanol was hydrogenated at normal pressure and at room temperature with 3 parts of palladium-on-charcoal catalyst 10%. After the calculated amount of hydrogen was taken up, the catalyst was filtered off and the filtrate was evaporated. The residue was distilled twice, yielding 23 parts (100%) of ethyl 2-methyl-1-piperazinecarboxylate; bp. 95°-98° C. at 66.5 pa (int. 37).

(c) A mixture of 14 parts of 3-[5-chloro-1-(4-fluorophenyl)pentyl]pyridine, 7.75 parts of ethyl 2-methyl-1-piperazinecarboxylate, 8.7 parts of N,N-diethylethanamine, 0.1 parts of potassium iodide and 198 parts of N,N-dimethylformamide was stirred for 40 hours at 70° C. The reaction mixture was evaporated and the residue was taken up in a mixture of water and sodium carbonate. The aqueous layer was extracted with trichloromethane. The extract was washed with a sodium carbonate solution in water and water, dried, filtered and evaporated. The residue was purified by column chromatography over silica gel using a mixture of trichloromethane and methanol (98:2 by volume) as eluent. The pure fractions were collected and the eluent was evaporated, yielding 18 parts (96.7%) of ethyl 4-[5-(4-fluorophenyl)-5-(3-pyridinyl)pentyl]-2-methyl-1-piperazinecarboxylate as a residue (int. 38).

(d) A mixture of 12 parts of ethyl 4-(5-(4-fluorophenyl)-5-(3-pyridinyl)pentyl]-2-methyl-1-piperazinecarboxylate, 16 parts of potassium hydroxide and 128 parts of 2-propanol was stirred for 4 days at reflux temperature. After cooling, the reaction mixture was evaporated. Water was added to the residue and the mixture was evaporated till all traces of 2-propanol were removed (this was repeated twice). The residue was taken up in water and the product was extracted with dichloromethane. The extract was washed with water, dried, filtered and evaporated. The residue was purified by column chromatography over silica gel using a mixture of trichloromethane and methanol, saturated with ammonia, (95:5 by volume) as eluent. The pure fractions were collected and the eluent was evaporated, yielding 6.7 parts (67.6%) of 1-(5-(4-fluorophenyl)-5-(3-pyridinyl)pentyl]-3-methylpiperazine as a residue (int. 39).

In a similar manner there was also prepared:
1-[5,5-bis(4-fluorophenyl)pentyl]-3-methylpiperazine (int. 40).

Example 8

(a) To a stirred solution of 49.5 parts of 3-methyl-1-(phenylmethyl) piperazine in 1350 parts of trichloromethane was added dropwise a solution of 63.3 parts of bis(1,1'-dimethylethyl)dicarbonate in 150 parts of trichloromethane at room temperature. Upon complete addition, stirring was continued overnight at room temperature. The reaction mixture was washed with water, dried, filtered and evaporated, yielding 85 parts (100%) of (1,1-dimethylethyl) 2-methyl-4-(phenylmethyl)-1-piperazinecarboxylate as a residue (int. 41).

(b) A mixture of 85 parts of (1,1-dimethylethyl) 2-methyl-4-(phenylmethyl)-1-piperazinecarboxylate and 400 parts of methanol was hydrogenated at normal pressure and at room temperature with 3 parts of palladium-on-charcoal catalyst 10%. After the calculated amount of hydrogen was taken up, the catalyst was filtered off and the filtrate was evaporated, yielding 55 parts (94.6%) of (1,1-dimethylethyl) 2-methyl-1-piperazinecarboxylate as a residue (int. 42).

(c) A mixture of 5 parts of N-(4-chlorobutyl)-N-(4-fluorophenyl)-3-pyridinecarboxamide, 2.77 parts of (1,1-dimethylethyl) 2-methyl-1-piperazinecarboxylate, 1.58 parts of sodium carbonate and 94 parts of N,N-dimethylformamide was stirred for 48 hours at 90° C. The reaction mixture was evaporated and the residue was taken up in water. The product was extracted twice with dichloromethane. The combined extracts were washed with water, dried, filtered and evaporated. The residue was purified by column chromatography over silica gel using a mixture of trichloromethane and methanol (96:4 by volume) as eluent. The first fraction was collected and the eluent was evaporated, yielding 3.5 parts (57.2%) of (1,1-dimethylethyl) 4-[4-[(4-fluorophenyl)(3-pyridinylcarbonyl)amino]butyl]-2-methyl-1-piperazinecarboxylate as a residue (int. 43).

(d) To a stirred solution of 3.5 parts of (1,1-dimethylethyl) 4-[4-[(4-fluorophenyl)(3-pyridinylcarbonyl)amino]butyl]-2-methyl-1-piperazinecarboxylate in 80 parts of methanol was bubbled gaseous hydrogen chloride. The reaction mixture was stirred for 10 minutes at reflux temperature and evaporated. The residue was taken up in water and the whole was treated with an ammonium hydroxide solution. The product was extracted twice with dichloromethane. The combined extracts were dried, filtered and evaporated, yielding 2.48 parts (90.4%) of N-(4-fluorophenyl)-N-[4-(3-methyl-1-piperazinyl)butyl]-3-pyridinecarboxamide as a residue (int. 44).

In a similar manner there was also prepared:

4-fluoro-N-[4-(3-methyl-1-piperazinyl)butyl]-N-(3-pyridinyl)benzamide as a residue (int. 45).

Example 9

To a stirred and refluxed Grignard complex, previously prepared starting from 11.34 parts of bromomethane in 135 parts of tetrahydrofuran and 2.87 parts of magnesium was added dropwise a solution of 9.31 parts of ethyl 4-(phenylmethyl)-2-piperazinecarboxylate in 135 parts of tetrahydrofuran was added dropwise to the thus obtained reaction mixture. Upon complete addition, the whole was stirred and refluxed for 2 hours. After cooling, the mixture was poured into a mixture of crushed ice and concentrated hydrochloric acid. The whole was treated with concentrated ammonium hydroxide. The layers were separated and the aqueous layer was extracted with dichloromethane. The combined organic layers were dried, filtered and evaporated. The residue was purified by column chromatography over silica gel using a mixture of trichloromethane and methanol, saturated with ammonia, (95:5 by volume) as eluent. The pure fractions were collected and the eluent was evaporated, yielding 2.7 parts (38.4%) of $\alpha,\alpha$-dimethyl-4-(phenylmethyl)-2-piperazinemethanol as a residue (int. 46).

A mixture of 6.4 parts of $\alpha,\alpha$-dimethyl-4-(phenylmethyl)-2-piperazinemethanol and 50 parts of poly(phosphoric acid) was stirred for 1 hour at 140° C. After cooling, ice water was added and the whole was treated with a sodium hydroxide solution 50%. The product was extracted twice with dichloromethane. The combined extracts were washed with water, dried, filtered and evaporated, yielding 5 parts (85.6%) of 3-(1-methylethenyl)-1-(phenylmethyl)piperazine as a residue (int. 47).

Following the procedures described in example 8 intermediate 47, 3-(1-methylethenyl)-1-(phenylmethyl)piperazine was converted into 1-[5,5-bis(4-fluorophenyl)pentyl]-3-(1-methylethyl)piperazine as a residue (int. 48).

Example 10

(a) To a stirred and refluxing Grignard complex previously prepared starting from 280 parts of 1-bromo-4-fluorobenzene, 34.6 parts of magnesium and 392 parts of 1,1'-oxybisethane, was added dropwise a solution of 116 parts of ethyl 5-bromopentanoate in 392 parts of 1,1'-oxybisethane. Upon complete addition, stirring was continued for 4 hours at reflux temperature. The reaction mixture was decomposed with a saturated ammonium chloride solution and the product was extracted with 1,1'-oxybisethane. The extract was dried, filtered and evaporated. The residue was triturated in hexane. The latter was decanted and the residue was crystallized from hexane. The product was filtered off and dried at room temperature, yielding 100 parts of $\alpha$-(4-bromobutyl)-4-fluoro-$\alpha$-(4-fluorophenyl)benzenemethanol; mp. 55° C. (int. 49).

(b) A mixture of 100 parts of $\alpha$-(4-bromobutyl)-4-fluoro-$\alpha$-(4-fluorophenyl)benzenemethanol and 714 parts of concentrated hydrochloric acid was stirred and refluxed for 5 hours. The reaction mixture was cooled and the product was extracted with 2,2'-oxybispropane. The extract was dried, filtered and evaporated, yielding 92 parts of 1,1'-(5-bromo-1-penten-1-ylidene)bis[4-fluorobenzene] as a residue (int. 50).

(c) A mixture of 92 parts of 1,1'-(5-bromo-1-penten-1-ylidene)bis [4-fluorobenzene] and 400 parts of methanol was hydrogenated at normal pressure and at room temperature with 5 parts of palladium-on-charcoal catalyst 10%. After the calculated amount of hydrogen was taken up, the catalyst was filtered off and the filtrate was evaporated, yielding 84 parts of 1,1'-(5-bromo-1-pentylidene)bis[4-fluorobenzene] as a residue (int. 51).

Following the same procedures there was further prepared:
1,1'-(5-bromo-1,1-pentanediyl)bis[4-methoxybenzene] as a residue (int. 52).

Example 11

(a) A mixture of 4.8 parts of a sodium hydride dispersion 50% and 250 parts of dimethyl sulfoxide was stirred for 30 minutes at 60° C. under nitrogen atmosphere. 21.45 parts of (3-carboxypropyl)triphenylphosphonium bromide were added portionwise to the mixture at room temperature (exothermic reaction, the temperature rose from 24° C. to 32° C.). Upon complete addition, stirring was continued for 15 minutes at room temperature. To the thus obtained solution there were added portionwise 10.05 parts of (4-fluorophenyl)(3-pyridinyl)methanone at room temperature. Upon completion, stirring was continued overnight at room temperature. The reaction mixture was poured into ice water and the whole was acidified with a hydrochoric acid solution 36% to pH 2. The separated aqueous layer was washed twice with methylbenzene and treated with concentrated ammonium hydroxide to pH 5. The product was extracted twice with trichloromethane. The combined extracts were dried, filtered and evaporated. The residue was purified by column chromatography over silica gel using a mixture of trichloromethane and methanol (95:5 by volume) as eluent. The pure fraction was collected and the eluent was evaporated, yielding 6.3 parts (46.6%) of (E+Z)-5-(4-fluorophenyl)-5-(3-pyridinyl)-4-pentenoic acid as a residue (int. 53).

(b) A mixture of 22 parts of (E+Z)-5-(4-fluorophenyl)-5-(3-pyridinyl)-4-pentenoic acid, 8.0 parts of concentrated sulfuric acid, 68.4 parts of 2,2-dimethoxypropane and 320 parts of methanol was stirred for 3 hours at reflux temperature. After cooling, the reaction mixture was treated with methanol, saturated with ammonia. The reaction mixture was evaporated and the residue was purified by column chromatography over silica gel using a mixture of trichloromethane and methanol (95:5 by volume) as eluent. The pure fractions were collected and the eluent was evaporated, yielding 10 parts (43.8%) of methyl (E+Z)-5-(4-fluorophenyl)-5-(3-pyridinyl)-4-pentenoate as a residue (int. 54).

(c) A mixture of 4.6 parts of methyl (E+Z)-5-(4-fluorophenyl)-5-(3-pyridinyl)-4-pentenoate, 1 part of a solution of thiophene in methanol 4% and 200 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated, yielding 4 parts (95.3%) of methyl $\epsilon$-(4-fluorophenyl)-3-pyridinepentanoate as a residue (int. 55).

(d) To a stirred (under nitrogen atmosphere) mixture of 6 parts of methyl $\epsilon$-(4-fluorophenyl)-3-pyridinepentanoate and 67.5 parts of tetrahydrofuran were added dropwise 30 parts of a solution of borane, compound with thiobismethane, in tetrahydrofuran. Upon complete addition, stirring was continued for 20 hours at reflux temperature. After cooling, 60 parts of methanol were added dropwise carefully. Upon completion, stirring was continued [or 1 hour at reflux. After evaporation, the residue was purified by column chromatography over silica gel using a mixture of trichloromethane and methanol (97:3 by volume) as eluent. The pure fraction was collected and the eluent was evaporated, yielding 4 parts (73.4%) of ε-(4-fluorophenyl)-3-pyridinepentanol as a residue (int. 56).

(e) 64 Parts of thionyl chloride were added portionwise to 4 parts of ε-(4-fluorophenyl)-3-pyridinepentanol. Upon complete addition, stirring was continued for 2 hours at reflux temperature. The reaction mixture was evaporated and the residue was taken up in water. The whole was treated with sodium carbonate. The product was extracted twice with methylbenzene. The combined extracts were washed with water, dried, filtered and evaporated, yielding 3.7 parts (100%) of 3-[5-chloro-1-(4-fluorophenyl)pentyl]pyridine as a residue (int. 57).

Example 12

(a) To a stirred and cooled (−20° C.) solution of 64 parts of methyl (E+Z)-5-(4-fluorophenyl)-5-(3-pyridinyl)-4-pentenoate in 540 parts of tetrahydrofuran were added 99 parts of a lithium tetrahydroaluminate solution 1M in tetrahydrofuran. After stirring for 15 minutes at this low temperature, the reaction mixture was decomposed with 70 parts of a saturated solution of a 2,3-dihydroxybutanedioc acid, sodium/potassium salts in water. The precipitate was filtered off and the filtrate was evaporated. The residue was purified by column chromatography (HpLC) over silica gel using a mixture of trichloromethane and methanol (98:2 by volume) as eluent. The first fraction was collected and the eluent was evaporated, yielding 10 parts (17.4%) of (E)-5-(4-fluorophenyl)-5-(3-pyridinyl)-4-penten-1-ol as a residue (int. 58). The second fraction was collected and the eluent was evaporated, yielding 20 parts (34.8%) of (Z)-5-(4-fluorophenyl)-5-(3-pyridinyl)-4-penten-1-ol as a residue (int. 59).

(b) 160 parts of thionyl chloride were added dropwise to 10 parts of (E)-5-(4-fluorophenyl)-5-(3-pyridinyl)-4-penten-1-ol while stirring (exothermic reaction, the temperature rose to 45° C.). Upon complete addition, stirring was continued for 2 hours at room temperature. The reaction mixture was evaporated. The residue was taken up in methylbenzene and the solvent was evaporated again. The residue was solidified in 2,2'-oxybispropane. The product was filtered off and dried, yielding 11.5 parts (94.4%) of (E)-3-[5-chloro-1-(4-fluorophenyl)-1-pentenyl]pyridine hydrochloride (int. 60).

In a similar manner there were also prepared:
(Z)-3-(5-chloro-1-(4-fluorophenyl)-1-pentenyl]pyridine (int. 61) and (E)-2-[5-chloro-1-(4-fluorophenyl)-1-pentenyl]pyridine (int. 62).

Example 13

(a) To a stirred solution of 60.3 parts of (4-fluorophenyl) (3-pyridinyl)methanone in 240 parts of methanol were added portionwise 17.1 parts of sodium borohydride. Upon completion, stirring was continued for 15 hours at room temperature. The reaction mixture was evaporated and 100 parts of water were added to the residue. Then there was added slowly a hydrochloric acid solution 4N till a clear solution was obtained. The acid phase was alkalized with a sodium hydroxide solution 10N and the product was extracted three times (1×200 and 2×100 parts) with dichloromethane. The combined extracts were dried, filtered and evaporated. The residue was converted into the hydrochloride salt in 2-propanol at room temperature. The salt was filtered off and dried, yielding 63 parts (87.6%) of α-(4-fluorophenyl)-3-pyridinemethanol hydrochloride; mp. 158.3° C. (int. 63)

(b) To a stirred and heated (50° C.) mixture of 15 parts of °-(4-fluorophenyl)-3-pyridinemethanol, 3.4 parts of N,N,N-triethylbenzenemethanaminium chloride, 50 parts of a sodium hydroxide solution 50% and 135 parts of methylbenzene were added dropwise 10 parts of 1-bromo-3-chloropropane. Upon complete addition, stirring was continued for 4 hours. Another portion of 5 parts of 1-bromo-3-chloropropane were added and the whole was stirred for 4 hours at 50° C. After cooling to room temperature, the reaction mixture was poured into ice water and the product was extracted twice with methylbenzene. The combined extracts were washed with a sodium carbonate solution, dried, filtered and evaporated. The excess of 1-bromo-3-chloropropane was distilled off at on oil pump. The residue was purified by column chromatography over silica gel using a mixture of trichloromethane and methanol, saturated with ammonia, (97:3 by volume) as eluent. The pure fractions were collected and the eluent was evaporated, yielding 6 parts (34.3%) of a mixture of 55% of 3-[(3-chloropropoxy)(4-fluorophenyl)methyl]pyridine and 45% of 3-[(3-chloropropoxy)(4-fluorophenyl)methyl]pyridine monohydrochloride as a residue (int. 64).

In a similar manner there was also prepared:
1,1'-[(3-chloropropoxy)methylene]bis[4-fluorobenzene] as a residue (int. 65).

Example 14

To a stirred mixture of 28.2 parts of 3-pyridinamine, 59 parts of N,N-diethylethanamine and 450 parts of methylbenzene were added dropwise 39 parts of 4-fluorobenzoyl chloride (exothermic reaction, the temperature rose to 40° C.). Upon complete addition, stirring was continued for 2 hours at reflux temperature. After cooling, the precipitated product was filtered off and dissolved in trichloromethane. The organic layer was washed twice with water, dried, filtered and evaporated. The residue was suspended in 2,2'-oxybispropane. The product was filtered off and dried, yielding 52.3 paris (80.6%) of 4-fluoro-N-(3-pyridinyl)benzamide; mp. 150.2° C. (int. 66).

(b) To a stirred solution of 21.6 parts of 4-fluoro-N-(3-pyridinyl) benzamide in 235 parts of N,N-dimethylformamide were added portionwise 5.76 parts of a sodium hydride dispersion 50% at <25° C. under nitrogen atmosphere. After stirring for 1.5 hours at room temperature, the mixture was cooled to 0° C. and 27.8 parts of 1-bromo-4-chlorobutane were added. The reaction mixture was stirred for 3 hours at 60° C. After cooling, the whole was poured into 1000 parts of ice water and the product was extracted twice with methylbenzene. The combined extracts were washed with water, dried, filtered and evaporated. The residue was purified by column chromatography over silica gel using a mixture of trichloromethane and methanol (99:1 by volume) as eluent. The pure fractions were collected and the eluent was evaporated, yielding 7.4 parts (24.1%) of N-(4-chlorobutyl)-4-fluoro-N-(3-pyridinyl)benzamide as a residue (int. 67).

In a similar manner there was also prepared:
N-(4-chlorobutyl)-N-(4-fluorophenyl)-3-pyridinecarboxamlde as a residue (int. 68).

Example 15

(a) A mixture of 35 parts of 4-fluoro-N-(4-fluorophenyl)benzenamine, 107 parts of 4-chlorobutanoyl chloride and 130 parts of methylbenzene was stirred for 2 hours at reflux temperature. The reaction mixture was washed with a sodium chloride solution, dried, filtered and evaporated. The residue was distilled to remove the excess of 4-chlorobutanoyl chloride, yielding 47 parts (95.0%) of 4-chloro-N,N-bis(4-fluorophenyl)butanamide as a residue (int. 69).

(b) To a stirred and cooled (0° C.) solution of 48 parts of 4-chloro-N,N-bis(4-fluorophenyl)butanamide in 108 parts of tetrahydrofuran were added 240 parts of a solution of borane, compound with thiobismethane, in tetrahydrofuran. After stirring overnight at room temperature, the reaction mixture was decomposed with 160 parts of methanol. After evaporation, the residue was purified by column chromatography over silica gel using a mixture of triohloromethane and petroleum ether (20:80 by volume) as eluent. The pure fractions were collected and the eluent was evaporated, yielding 32.5 parts (91.5%) of N-(4-chlorobutyl)-4-fluoro-N-(4-fluorophenyl)benzenamine as a residue (int. 70).

Example 16

To a stirred solution of 20 parts of 2,6-dimethyl-4-(phenylmethoxy)benzenamine and 270 parts of methylbenzene were added portionwise 10.9 parts of 2-chloroacetyl chloride (exothermic reaction, the temperature rose to 30° C.). Upon complete addition, the reaction mixture was stirred for 1 hour at reflux temperature. After cooling, the precipitated product was filtered off and dried, yielding 23.8 parts (89%) of 2-chloro-N-[2,6-dimethyl-4-(phenylmethoxy)phenyl]acetamide; mp. 165.3° C. (int. 71).

In a similar manner there were also prepared:
ethyl 3,5-dichloro-4-((2-chloroacetyl)amino)benzoate; mp. 182.0° C. (int. 72);
N-(2-acetyl-4-nitrophenyl)-2-chloroacetamide; mp. 161.5° C. (int. 73);
3,5-dichloro-4-((2-chloroacetyl)amino)-N,N-dimethylbenzamide; mp. 250.6° C. (int. 74);
N-(2-acetyl-4-cyanophenyl)-2-chloroacetamide (int. 75);
N-[2-acetyl-4-(dimethylamino)phenyl]-2-chloroacetamide (int. 76);
2-chloro-N-(2-chloro-3-pyridinyl)acetamide (int. 77);
2-chloro-N-(2,6-dichloro-3-pyridinyl)acetamide (int. 78);
N-(3-acetyl-2,6-dimethylphenyl)-2-chloroacetamide; mp. 131.4° C. (int. 79);
2-chloro-N-(3,5-dimethyl-4-pyridinyl)acetamide monohydrochloride (int. 80);
2-chloro-N-(4-methoxy-2,6-dimethylphenyl)acetamide; mp. 186.3° C. (int. 81);
2-chloro-N-(2,4,6-trimethyl-3-pyridinyl)acetamide monohydrochloride; mp. 200.0° C. (int. 82);
2-chloro-N-(5,6,7,8-tetrahydro-3-methyl-4-quinolinyl)acetamide monohydrochloride (int. 83);
2-chloro-N-(3-chloro-2,5,6,7-tetrahydro-2-oxo-1H-1-pyrindin-4-yl) acetamide (int. 84):
2-chloro-N-[2,6-dichloro-4-(dimethylamino)phenyl]acetamide monohydrochloride (int. 85):
2-chloro-N-[2,6-dichloro-4-[(1-methylethyl)amino]phenyl]acetamide monohydrochloride (int. 86);
2-chloro-N-(tetrahydro-2-oxo-1H-1-pyrindin-4-yl)acetamide (int. 87);
N-(3-bromo-5,6,7,8-tetrahydro-2-methyl-4-quinolinyl)-2-chloroacetamide; mp. 203.0° C. (int. 88);
N-(3-bromo-5-methyl-4-pyridinyl)-2-chloroacetamide (int. 89):
2-cbloro-N-(3-cbloro-5,6,7,8-tetrahydro-2-methyl-4-quinolinyl) acetamide; mp. 196.4° C. (int. 90);
2-chloro-N-(3,5-dichloro-4-pyridinyl)acetamide (int. 91);
N-(3-bromo-6,7-dihydro-5H-1-pyrindin-4-yl)-2-chloroacetamide (int. 92);
N-(3-bromo-5,6,7,8-tetrahydro-4-quinolinyl)-2-chloroacetamide (int. 93) and
N-(3-bromo-6,7,8,9-tetrahydro-5H-cyclohepta[b]pyridin-4-yl)-2-chloroacetamide as a residue (int. 94).

Example 17

(a) To a stirred solution of 50 parts of 3-(phenylazo)-2,4-pentanedione and 35 parts of ethanimidamide monohydrochloride in 711 parts of ethanol was added a solution of 8.5 parts of sodium in 126 parts of ethanol. After stirring overnight at room temperature, the precipitate was filtered off and the filtrate was stirred for 2 days at room temperature. The mixture was evaporated and the residue was diluted with a sodium hydroxide solution 10%. The separated aqueous layer was extracted with methylbenzene. The extract was dried, filtered and evaporated. The residue was purified by column chromatography over silica gel using a mixture of trichloromethane and methanol (98:2 by volume) as eluent. The pure fractions were collected and the eluent was evaporated with methylbenzene, yielding 7.5 parts (13.8%) of 4,6-dimethyl-5-(phenylazo)-2-pyridinamine as a residue (int. 95).

(b) A mixture of 7.5 parts of 4,6-dimethyl-5-(phenylazo)-2-pyridinamine and 200 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was purified by column chromatography over silica gel using a mixture of trichloromethane and methanol, saturated with ammonia (97:3 by volume) as eluent. The pure fractions were collected and the eluent was evaporated, yielding 3.3 parts (72.8%) of 4,6-dimethyl-2,5-pyridinediamine as a residue (int. 96).

(c) To a stirred solution of 3.3 parts of 4,6-dimethyl-2,5-pyridinediamine in 30 parts of acetic acid were added 4.7 parts of 2-chloroacetyl chloride at room temperature. The reaction mixture was stirred overnight at room temperature. The reaction mixture was diluted with methylbenzene and neutralised with sodium carbonate. The reaction mixture was filtered over diatomaceous earth and the filtrate was evaporated, yielding 2.6 parts (50.7%) of N-(6-amino-2,4-dimethyl-3-pyridinyl)-2-chloroacetamide as a residue (int. 97).

Example 18

A mixture of 20 parts of N-(4-amino-2,6-dichlorophenyl)acetamide, 10 parts of 2-propanone, 2 parts of a solution of thiophene in methanol 4%, 400 parts of methanol, 5 parts of potassium fluoride and 18 parts of 2-propanol, saturated with hydrogen chloride was hydrogenated in a Parr apparatus and at 50° C. with 2 parts of platinum-on-charcoal catalyst 5%. After the calculated amount of hydrogen was taken up, the catalyst was filtered off and the filtrate was evaporated. The residue was crystallized from acetonitrile. The product was filtered off and dried, yielding 15.7 parts (66.7%) of N-[2,6-dichloro-4-[(1-methylethyl)amino]phenyl]acetamide (int. 98).

Example 19

A mixture of 15.2 parts of N-(2-acetyl-4-nitrophenyl)acetamide, 5 parts of poly(oxymetbylene), 1 part of a solution of thiophene in methanol 4% and 200 parts of methanol was hydrogenated in a Parr apparatus and at 50° C. with 2 parts of palladium-on-charcoal catalyst 10%. After the calculated amount of hydrogen was taken up, the reaction mixture was evaporated. The residue was hydrogenated at normal pressure and at 50° C. in 6 parts of acetic acid. After the calculated amount of hydrogen was taken up, the catalyst was filtered off and the filtrate was evaporated. The residue was crystallized from methylbenzene. The product was filtered off and dried in vacuo at 40° C. yielding 10 parts (66.7%) of N-[2-acetyl-4-(dimethylamino) phenyl]acetamide as a residue (int. 99).

Example 20

(a) A mixture of 10.5 parts of 2-chloro-N-(2,6-dichloro-4-cyanophenyl) acetamide, 22 parts of 2-propanol, saturated with hydrogen chloride and 200 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was taken up in water and treated with a sodium hydroxide solution 50%. The product was extracted twice with dichloromethane. The combined extracts were dried, filtered and evaporated, yielding 10.7 parts (100%) of N-[4-(aminomethyl)-2,6-dichlorophenyl]-2-chloroacetamide as a residue (int. 100).

(b) 10.1 Parts of bis(1,1-dimethylethyl) dicarbonate were added dropwise to 10.7 parts of N-[4-(aminomethyl)-2,6-dichlorophenyl]-2-chloroacetamide. Upon complete addition, stirring was continued for 1 hour at room temperature. The reaction mixture was washed with water, dried, filtered and evaporated. The residue was crystallized from methylbenzene. The product was filtered off and dried, yielding 10.08 parts (62.3%) of (1,1-dimethylethyl) [[3,5-dichloro-4-[(2-chloroacetyl)amino]phenyl]methyl]carbamate (int. 101).

(c) A mixture of 7 parts of 4-[5,5-bis(4-fluorophenyl)pentyl]-2-piperazinecarboxamide, 6.6 parts of (1,1-dimethylethyl) [[3,5-dichloro-4-[(2-chloroacetyl)amino]phenyl)methyl)carbamate, 2.8 parts of N,N-diethylethanamine and 94 parts of N,N-dimethylformamide was stirred over weekend at 70° C. The reaction mixture was evaporated and the residue was taken up in water. The product was extracted twice with dichloromethane. The combined extracts were washed with water, dried, filtered and evaporated. The residue was purified by column chromatography over silica gel using a mixture of trichloromethane and methanol, saturated with ammonia, (96:4 by volume) as eluent. The desired fractions were collected and the eluent was evaporated, yielding 8.7 parts (80.7%) of (1,1-dimethylethyl) [[4-[[2-[2-(aminocarbonyl)-4-[5,5-bis(4-fluorophenyl)pentyl]-1-piperazinyl]acetyl]amino]-3,5-dichlorophenyl]methyl]carbamate as a residue (int. 102).

Example 21

(a) A mixture of 15 parts of 6,7,8,9-tetrahydro-4-nitro-5H-cyclohepten[b]pyridin,N-oxide and 320 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was stirred in 2,2′-oxybispropane. The product was filtered off and dried, yielding 10.73 parts (91.8%) of 6,7,8,9-tetrahydro-5H-cyclohepten[b]pyridin-4-amine as a residue (int. 103).

In a similar manner there was also prepared:
5,6,7,8-tetrahydro-3-methyl-4-quinolinamine as a residue (int. 104).

(b) To a stirred solution of 10.7 parts of 6,7,8,9-tetrahydro-5H-cyclohepten[b]pyridin-4-amine in 170 parts of acetic acid were added dropwise 16 parts of bromine at room temperature. Upon complete addition, stirring was continued overnight. The reaction mixture was evaporated and the residue was taken up in water. The aqueous solution was treated with an ammonium hydroxide solution and the product was extracted twice with dichloromethane. The combined extracts were dried, filtered and evaporated. The residue was purified by column chromatography over silica gel using a mixture of trichloromethane and methanol, saturated with ammonia, (98:2 by volume) as eluent. The pure fractions were collected and the eluent was evaporated, yielding 8.2 parts (51.5%) of 3-bromo-6,7,8,9-tetrahydro-5H-cyclohepta[b]pyridin-4-amine as a residue (int. 105).

In a similar manner there were also prepared:
3-bromo-6,7-dihydro-5H-1-pyrindin-4-amine (int. 106):
3-chloro-5,6,7,8-tetrahydro-2-methyl-4-quinolinamine (int. 107):
3-bromo-5,6,7,8-tetrahydro-4-quinolinanine (int. 108) and
3-bromo-5, 6,7,8-tetrahydro-2-methyl-4-quinolinamine; mp. 176.8° C. (int. 109).

Appropriate starting materials for said procedure were described in Eur. Pat. No. 860,723.

Example 22

A mixture of 9 parts of 4-amino-N,N-dimethylbenzamide, 137 parts of concentrated hydrochloric acid and 90 parts of water was stirred at room temperature. 21.6 Parts of a hydrogen peroxide solution 30% in water were added and the whole was stirred for 4 hours at room temperature. The product was extracted three times with dichloromethane. The combined extracts were dried, filtered and evaporated. The residue was purified by column chromatography over silica gel using a mixture of trichloromethane and methanol (98:2 by volume) as eluent. The pure fractions were collected and the eluent was evaporated. The residue was crystallized from 2,2′-oxybispropane. The product was filtered off and dried, yielding 5.78 parts (46%) of 4-amino-3,5-dichloro-N,N-dimethylbenzamide; mp. 134.2° C. (int. 110).

Example 23

A mixture of 40 parts of N-(3-acetyl-2,6-dimethylphenyl)acetamide and 300 parts of concentrated hydrochloric acid was stirred for 20 hours at reflux temperature. After cooling, the reaction mixture was treated with ammonium hydroxide. The product was extracted twice with dichloromethane. The combined extracts were washed with water, dried, filtered and evaporated, yielding 35.5 parts (100%) of 1-(3-amino-2,4-dimethylphenyl)ethanone as a residue (int. 111).

In a similar manner there were also prepared:

1-[2-amino-5-(dimethylamino)phenyl]ethanone (int. 112) and
3,5-dichloro-N¹-(1-methylethyl)-1,4-benzenediamine (int. 113).

Example 24

15.7 parts of N-(2-acetyl-4-cyanophenyl)-2-chloroacetamide were added portionwise to 146.4 parts of concentrated sulfuric acid at room temperature. Upon complete addition, stirring was continued overnight at room temperature. The reaction mixture was poured into 500 parts of crushed ice while stirring. The precipitated product was filtered off and suspended in water. The precipitated product was filtered off, washed with water and suspended in 20 parts of acetonitrile. The product was filtered off, boiled in 20 parts of acetonitrile and filtered off, after cooling, yielding 10.4 parts (61.6%) of 3-acetyl-4-((2-chloroacetyl)amino]benzamide (int. 114).

B. Preparation of final compounds

Example 25

A mixture of 5.9 parts of 1,1'-(5-bromo-1-pentylidene)bis[4-fluorobenzene], 5.6 parts of N-(4-acetyl-2,6-dichlorophenyl)-3-(aminocarbonyl)-1-piperazineacetamide, 4.05 parts of N,N-diethylethanamine and 90 parts of N,N-dimethylformamide was stirred over weekend at 70° C. After evaporation, the residue was taken up in dichloromethane. The organic layer was washed with water, dried, filtered and evaporated. The residue was purified by column chromatography over silica gel using a mixture of trichloromethane and methanol (97:3 by volume) as eluent. The pure fractions were collected and the eluent was evaporated. The residue was converted into the hydrochloride salt in acetonitrile and 2-propanol. The salt was filtered off and dried, yielding 2.54 parts (24.0%) of N-(4-acetyl-2,6-dichlorophenyl)-3-(aminocarbonyl)-4-[5,5-bis(4-fluorophenyl)pentyl]-1-piperazineacetamide dihydrochloride; mp. 181.2° C. (compound 14).

Example 26

A mixture of 3.5 parts of 1,1'-(5-chloro-1-pentylidene)bis[4fluorobenzene], 2.94 parts of 3-(aminocarbonyl)-N-(5-fluoro-2-methylphenyl)-1-piperazineacetamide, 2.1 parts of N,N-diethylethanamine, 0.1 parts of potassium iodide and 45 parts of N,N-dimethylformamide was stirred and heated for 48 hours at about 70° C. After 24 hours of stirring 2.12 parts of sodium carbonate were added. The reaction mixture was evaporated. The residue was taken up in water and the product was extracted with dichloromethane. The extract was washed with water, dried, filtered and evaporated. The residue was purified by column chromatography over silica gel using a mixture of trichloromethane and methanol (95:5 by volume) as eluent. The pure fractions were collected and the eluent was evaporated. The residue was converted into the hydrochloride salt in acetonitrile, 2-propanol and a few drops of water. The salt was filtered off and dried over weekend at 100° C., yielding 1.70 parts of 3-(aminocarbonyl)-4-[5,5-bis (4-fluorophenyl)pentyl]-N-(5-fluoro-2-methylphenyl)-1-piperazineacetamide monohydrochloride; mp. 217.8° C. (compound 3).

Example 27

A mixture of 2.07 parts of N-(4-chlorobutyl)-4-fluoro-N-(4-fluorophenyl)benzenamine, 2.5 parts of N-(4-acetyl-2,6-dichlorophenyl)-3-[(methylamino)carbonyl]-1-piperazineacetamide, 1.3 parts of N,N-diethylethanamine and 97 parts of 2-methoxyethanol was stirred for 3 days at 70° C. The reaction mixture was evaporated and the residue was taken up in water. The product was extracted twice with dichloromethane. The combined extracts were washed with water, dried, filtered and evaporated. The residue was purified by column chromatography over silica gel using a mixture of trichloromethane and methanol (98:2 by volume) as eluent. The desired fraction was collected and the eluent was evaporated. The residue was crystallized from acetonitrile. The product was filtered off and dried, yielding a first fraction of 0.74 parts (19.0%) of N-(4-acetyl-2,6-dichlorophenyl)-4-[4-[bis(4-fluorophenyl)amino]butyl]-3-[(methylamino)carbonyl]-1-piperazineacetamide mp. 87.1° C. The second fraction was collected and the eluent was evaporated. The residue was crystallized from acetonitrile. The product was filtered off and dried, yielding a second fraction of 0.78 parts (20.1%) of N-(4-acetyl-2,6-dichlorophenyl)-4-[4-[bis(4-fluorophenyl)amino]butyl]3-[(methylamino)carbonyl]-1-piperazineacetamide; mp. 85.0° C. Total yield: 1.52 parts (39.1%) of N-(4-acetyl-2,6-dichlorophenyl)-4-[4-[bis(4-fluorophenyl)amino]butyl]-3-[(methylamino)carbonyl]-1piperazineacetamide (compound 97).

Example 28

A mixture of 4.72 parts of 3-[5-chloro-1-(4-fluorophenyl)pentyl]pyridine, 5.62 parts of 3-(aminocarbonyl)-N-[4-(aminocarbonyl)-2,6-dichlorophenyl]-1-piperazineacetamide, 1.58 parts of sodium carbonate, 0.1 parts of potassium iodide and 90 parts of N,N-dimethylacetamide was stirred for 48 hours at ±90° C. After evaporation, the residue was taken up in water and the product was extracted twice with dichloromethane. The combined extracts were washed with water, dried, filtered and evaporated. The residue was purified by column chromatography over silica gel using a mixture of trichloromethane and methanol, saturated with ammonia, (93:7 by volume) as eluent. The first fraction was collected and the eluent was evaporated. The residue was converted into the hydrochloride salt in 2-propanol. The salt was filtered off and dried, yielding 2.3 parts (20.9%) of 3-(aminocarbonyl)-N-[4-(aminocarbonyl)-2,6-dichlorophenyl]-4-[5-(4-fluorophenyl)-5-(3-pyridinyl)pentyl]-1-piperazineacetamide trihydrochloride,dihydrate; mp. 173.0° C. (compound 43).

Example 29

A mixture of 1.86 parts of 1,1'-(5-bromo-1-penten-1-ylidene)bis(4-fluorobenzene], 1.50 parts of N-(2-acetylphenyl)-3-(aminocarbonyl)-1-piperazineacetamide, 0.80 parts of sodium carbonate and 90 parts of N,N-dimethylformamide was stirred for 20 hours at 80° C. The reaction mixture was evaporated and the residue was taken up in water. The product was extracted twice with dichloromethane. The combined extracts were washed with water, dried, filtered and evaporated. The residue was purified by column chromatography over silica gel using a mixture of trichloromethane and methanol, saturated with ammonia, (97:3 by volume) as eluent. The pure fractions were collected and the eluent was evaporated. The residue was crystallized from 2,2'-oxybispropane, yielding 2.07 parts (73.9%) of N-(2-acetylphenyl)-3-(aminocarbonyl)-4-[5,5-bis(4-fluorophenyl)-4-pentenyl]-1-piperazineacetamide; mp. 110.7° C. (compound 18).

Example 30

A mixture of 3.6 parts of 1-(5,5-bis(4-fluorophenyl)-pentyl]-3-methylpiperazine, 3 parts of N-(4-acetyl-2,6-dichlorophenyl)-2-chloroacetamide, 1.9 parts of N,N-diethylethanamine and 45 parts of N,N-dimethylformamide was stirred for 20 hours at 70° C. The reaction mixture was evaporated and the residue was taken up in a mixture of sodium carbonate and water. The product was extracted with dichloromethane. The extract was washed with water, dried, filtered and evaporated. The residue was purified by column chromatography over silica gel using a mixture of trichloromethane and methanol (98:2 by volume) as eluent. The pure fractions were collected and the eluent was evaporated. The residue was converted into the hydrochloride salt in 2-propanol and 2,2'-oxybispropane. The product was filtered off and dried in vacuo at 40° C., yielding 1.74 parts (22.8%) of N-(4-acetyl-2,6-dichlorophenyl)-4-[5,5-bis(4-fluorophenyl)pentyl]-2-methyl-1-piperazineacetamide dihydrochloride,2-propanol(1:1),sesquihydrate; mp. 176.3° C. (compound 54).

Example 31

A mixture of 6.1 parts of 1-[5,5-bis(4-fluorophenyl)-pentyl]-2-piperazinecarboxamide, 4.3 parts of 2-chloro-N-(2,4,6-trimethyl-3-pyridinyl)acetamide monohydrochloride, 3.7 parts of sodium carbonate and 90 parts of N,N-dimethylformamide was stirred for 15 hours at 70° C. The reaction mixture was filtered, washed with N,N-dimethylformamide and the filtrate was evaporated in vacuo. The residue was purified by column chromatography over silica gel using a mixture of trichloromethane and methanol (92.5:7.5 by volume) as eluent. The pure fractions were collected and the eluent was evaporated. The residue was further purified by column chromatography over silica gel using a mixture of trichloromethane and methanol (90:10 by volume) as eluent. The pure fractions were collected and the eluent was evaporated. The residue was converted into the hydrochloride salt in 2-propanone and 2-propanol. The salt was filtered off, washed twice with 2-propanone and once with 2,2'-oxybispropane and dried . overnight at 100°-110° C., yielding 6.58 parts (61.2%) of 3-(aminocarbonyl)-4-[5,5bis(4-fluorophenyl)pentyl]-N-(2,4,6-trimethyl-3-pyridinyl)-1-piperazineacetamide trihydrochloride,hemihydrate; mp. 224.7° C. (compound 115).

Example 32

A mixture of 5.04 parts of 4-[5,5-bis(4-fluorophenyl)-pentyl]-2-piperazinecarboxamide, 2.9 parts of 2-chloro-N-(5-fluoro-2-methylphenyl) acetamide, 2.1 parts of sodium carbonate, 0.1 parts of potassium iodide and 120 parts of 4-methyl-2-pentanone was stirred and refluxed for 18 hours. After cooling, the reaction mixture was washed with water. The organic layer was dried, filtered and evaporated. The residue was purified by column chromatography over silica gel using a mixture of trichloromethane and methanol (95:5 by volume) as eluent. The pure fractions were collected and the eluent was evaporated. The residue was converted into the hydrochloride salt in acetonitrile and 2-propanol. The precipitate was filtered off and the filtrate was evaporated. The residue was dried at 80° C., yielding 5.48 parts (71%) of 2-(aminocarbonyl)-4-[5,5-bis(4-fluorophenyl)pentyl]-N-(5-fluoro-2-methylphenyl)-1-piperazineacetamide monohydrochloride; mp. 148.2° C. (compound 9).

Example 33

A mixture of 7 parts of 3-(aminocarbonyl)-4-[5,5-bis(4-fluorophenyl)pentyl]-N-(2,6-dichloro-4-nitrophenyl)-1-piperazineacetamide, 1 part of a solution of thiophene in methanol 4% and 120 parts of methanol was hydrogenated in a Parr apparatus and at 50° C. with 2 parts of platinum-on-charcoal catalyst 5%. After the calculated amount of hydrogen was taken up, the catalyst was filtered off and the filtrate was evaporated. The residue was converted into the hydrochloride salt in 2-propanol and acetonitrile. The salt was filtered off and dried, yielding 5.55 parts (77.7%) of 3-(aminocarbonyl)-N-(4-amino-2,6-dichlorophenyl)-4-[5,5-bis(4-fluorophenyl)pentyl]-1-piperazineaceiamide trihydrochloride; mp. 190.8° C. (compound 84).

Example 34

A mixture of 4.8 parts of N-(2-acetyl-4-aminophenyl)-4-[5,5-bis(4fluorophenyl)pentyl]-2-methyl-1-piperazineacetamide. 3 parts of poly(oxymethylene), 1 part of a solution of thiophene in methanol 4% and 120 parts of methanol was hydrogenated in a Parr apparatus and at 50° C. with 2 parts of palladium-on-charcoal catalyst 10%. After the calculated amount of hydrogen was taken up, the catalyst was filtered off and the filtrate was evaporated. The residue was purified by column chromatography over silica gel using a mixture of trichloromethane and methanol (95:5 by volume) as eluent. The desired fraction was collected and the eluent was evaporated. The residue was converted into the hydrochloride salt in 2-propanol and 2,2'-oxybispropane. The salt was filtered off and dried, yielding 1.47 parts (25.1%) of N-(2-acetyl-4-(dimethylamino)phenyl]-4-[5,5-bis(4-fluorophenyl)pentyl]2-methyl-1-piperazineacetamide dihydrochloride; mp. 122.0° C. (compound 83).

Example 35

A mixture of 5.2 parts of 4-[5,5-bis(4-fluorophenyl)-pentyl]-N-[2,6-dimethyl-4-(phenylmethoxy)phenyl]-2-methyl-1-piperazineacetamide and 120 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was converted into the hydrochloride salt in acetonitrile and 2-propanol. The salt was filtered off and dried, yielding 2.72 parts (56%) of 4-[5.5-bis(4-fluorophenyl)pentyl]-N-(4-hydroxy-2,6-dimethylphenyl)-2-methyl-1-piperazineacetamide dihydrochloride,hemihydrate; mp. 174.2° C. (compound 36).

Example 36

To a stirred solution of 4.5 parts of N-(2-acetyl-4-aminophenyl)3-(aminocarbonyl)-4-(5,5-bis(4-fluorophenyl)pentyl)-1-piperazineacetamide in 60 parts of trichloromethane were added 1.17 parts of N,N-diethylethanamine. A solution of 0.78 parts of propanoyl chloride in 45 parts of trichloromethane was added dropwise at room temperature (slightly exothermic reaction, the temperature rose from 24° C. to 30° C.). Upon completion, the whole was stirred for 3 hours at room temperature. The separated organic layer was washed with a sodium carbonate solution in water and water, dried, filtered and evaporated. The residue was crystallized from acetonitrile. After cooling to 0° C., the product was filtered off and dried in vacuo, first at 50° C. and then at 100° C., yielding 2.93 parts (57.7%) of N-[2-acetyl-4-[(1-oxopropyl)amino]phenyl]-3-(aminocarbonyl)-4-[5,5-bis(4-fluorophenyl) pentyl]-1-piperazineacetamide; mp. 163.4° C. (compound 32).

Example 37

To a stirred solution of 4.5 parts of N-(4-amino-2,6-dichlorophenyl)-4-[5,5-bis(4-fluorophenyl)pentyl]-2-methyl-1-piperazineacetamide in 60 parts of acetic acid was added dropwise a solution of 1.02 parts of potassium cyanate in 17 parts of water. Upon completion, stirring was continued overnight at room temperature. The reaction mixture was evaporated and the residue was taken up in water. The whole was treated with an ammonium hydroxide solution and the product was extracted twice with dichloromethane. The combined extracts were washed with water, dried, filtered and evaporated. The residue was purified by column chromatography over silica gel using a mixture of trichloromethane and methanol, saturated with ammonia, (96:4 by volume) as eluent. The second fraction was collected and the eluent was evaporated. The residue was suspended in 2,2'-oxybispropane. The product was filtered off and dried, yielding 2.49 parts (51.9%) of N-[4-[(aminocarbonyl)amino]-2,6-dichlorophenyl]-4-[5,5-bis(4-fluorophenyl)pentyl]-2-methyl-1-piperazineacetamide; mp. 119.9° C. (compound 76).

Example 38

A mixture of 8.7 parts of (1,1-dimethylethyl) [[4-[[2-[2-(aminocarbonyl)-4-[5,5-bis(4-fluorophenyl)pentyl]-1-piperazinyl]acetyl]amino]-3,5-dichlorophenyl]methyl]carbamate, 120 parts of methanol and 24 parts of 2-propanol, saturated with hydrogen chloride was stirred for 30 minutes at reflux temperature. The reaction mixture was evaporated and the residue was taken up in water. The whole was treated with an ammonium hydroxide solution and the product was extracted twice with dichloromethane. The combined extracts were washed with water, dried, filtered and evaporated. The residue was purified by column chromatography over silica gel using a mixture of trichloromethane and methanol, saturated with ammonia, (93:7 by volume) as eluent. The desired fraction was collected and the eluent was evaporated. The residue was suspended in 2,2'-oxybispropane. The product was filtered off and dried, yielding 3.34 parts (44.9%) of 2-(aminocarbonyl)-N-(4-(aminomethyl)-2,6-dichlorophenyl]-4-[5,5-bis(4-fluorophenyl)pentyl]-1-piperazineacetamide; mp. 160.8° C. (compound 100).

All other compounds listed in tables 1 and 2 were obtained by analgous methods of preparation as described in examples 25-38, the actual method of preparation being indicated in column 2 ("Ex. No.").

TABLE 1

$$Q-Alk-N\underset{X}{\bigcirc}N-C_mH_{2m}-\overset{O}{\underset{\|}{C}}-NH-\underset{R^{11}}{\bigcirc}R^{10}\text{ (with }R^9\text{)}$$

| Comp. No. | Ex. No. | Q—Alk— | X | m | R⁹ | R¹⁰ | R¹¹ | base/salt | mp. °C. |
|---|---|---|---|---|---|---|---|---|---|
| 1 | 26 | (4-F—C₆H₄)₂—CH—(CH₂)₄— | 3-CONH₂ | 1 | 2-Cl | 6-CH₃ | H | 2 HCl/0.5 H₂O | 206.7 |
| 2 | 28 | (4-F—C₆H₄)₂—CH—(CH₂)₄— | 3-CONH₂ | 1 | 2-OCH₃ | H | H | 2 HCl | 195.8 |
| 3 | 26 | (4-F—C₆H₄)₂—CH—(CH₂)₄— | 3-CONH₂ | 1 | 2-CH₃ | 5-F | H | HCl | 217.8 |
| 4 | 29 | (4-F—C₆H₄)₂—CH—(CH₂)₄— | 2-CH₂OH | 1 | 2-CH₃ | 6-CH₃ | H | HCl | 237.4 |
| 5 | 29 | (4-F—C₆H₄)₂—CH—(CH₂)₄— | 3-CONHCH₃ | 1 | 2-CH₃ | 6-CH₃ | H | 2 HCl/H₂O | 212.8 |
| 6 | 29 | (4-F—C₆H₄)₂—CH—(CH₂)₄— | 2-CON(CH₃)₂ | 1 | 2-CH₃ | 6-CH₃ | H | 2 HCl | 165.5 |
| 7 | 29 | (4-F—C₆H₄)₂—CH—(CH₂)₄— | 3-CH₂OH | 1 | 2-CH₃ | 6-CH₃ | H | 2 HCl | 207.3 |
| 8 | 30 | (4-F—C₆H₄)₂—CH—(CH₂)₄— | 2-CONH₂ | 1 | 2-Cl | H | H | HCl | 227.1 |
| 9 | 32 | (4-F—C₆H₄)₂—CH—(CH₂)₄— | 2-CONH₂ | 1 | 2-CH₃ | 5-F | H | HCl | 148.2 |
| 10 | 25 | (4-F—C₆H₄)₂—C=CH—(CH₂)₃— | 3-CONH₂ | 1 | 2-Cl | 4-CN | 6-Cl | base | 181.3 |
| 11 | 25 | (4-F—C₆H₄)₂—C=CH—(CH₂)₃— | 3-CONH₂ | 1 | 2-Cl | 6-Cl | H | base | 149.7 |
| 12 | 25 | (4-F—C₆H₄)₂—C=CH—(CH₂)₃— | 3-CONH₂ | 1 | 2-Cl | 4-COCH₃ | 6-Cl | 2 HCl/H₂O | 192.7 |
| 13 | 25 | (4-F—C₆H₄)₂—C=CH—(CH₂)₃— | 3-CONH₂ | 1 | 2-Cl | 4-COCH₃ | 6-Cl | base | 150.3 |
| 14 | 25 | (4-F—C₆H₄)₂—C=CH—(CH₂)₃— | 3-CONH₂ | 1 | 2-Cl | 4-Cl | 6-Cl | 2 HCl | 181.2 |
| 15 | 25 | (4-F—C₆H₄)₂—C=CH—(CH₂)₃— | 3-CONH₂ | 1 | 2-Cl | 4-Cl | 6-Cl | base | 179.4 |
| 16 | 25 | (4-F—C₆H₄)₂—C=CH—(CH₂)₃— | 3-CONH₂ | 1 | 2-Cl | 4-Cl | 6-Cl | 2 HCl | 175.4 |
| 17 | 30 | (4-F—C₆H₄)₂—C=CH—(CH₂)₃— | 2-CONH₂ | 1 | 2-Cl | 6-Cl | H | base | 157.7 |
| 18 | 29 | (4-F—C₆H₄)₂—C=CH—(CH₂)₃— | 3-CONH₂ | 1 | 2-COCH₃ | H | 6-Cl | base | 110.7 |
| 19 | 30 | (4-F—C₆H₄)₂—CH—(CH₂)₄— | 2-CONH₂ | 1 | 2-Cl | 4-CON(CH₃)₂ | H | base | 150.8 |
| 20 | 30 | (4-F—C₆H₄)₂—CH—(CH₂)₄— | 2-CONH₂ | 1 | 2-COCH₃ | 4-CONH₂ | 6-Cl | base | 149.9 |
| 21 | 30 | (4-F—C₆H₄)₂—CH—(CH₂)₄— | 2-CONH₂ | 1 | 2-COCH₃ | 4-COOC₂H₅ | 6-Cl | base | 124.3 |
| 22 | 30 | (4-F—C₆H₄)₂—CH—(CH₂)₄— | 3-CONH₂ | 1 | 2-COCH₃ | 4-CONH₂ | 6-Cl | base | 218.3 |
| 23 | 30 | (4-F—C₆H₄)₂—CH—(CH₂)₄— | 2-CONH₂ | 1 | 2-COCH₃ | 4-CN | H | base | 171.2 |
| 24 | 30 | (4-F—C₆H₄)₂—C=CH—(CH₂)₃— | 2-CONH₂ | 1 | 2-COCH₃ | 4-NO₂ | H | base | 135.1 |
| 25 | 31 | (4-F—C₆H₄)₂—C=CH—(CH₂)₃— | 2-CONH₂ | 1 | 2-COCH₃ | H | H | 2 HCl | 160.4 |
| 26 | 33 | (4-F—C₆H₄)₂—CH—(CH₂)₄— | 3-CONH₂ | 1 | 2-COCH₃ | 4-NH₂ | H | base | 141.2 |
| 27 | 30 | (4-F—C₆H₄)₂—CH—(CH₂)₄— | 3-CONH₂ | 1 | 2-COCH₃ | 4-N(CH₃)₂ | H | base | 115.0 |
| 28 | 30 | (4-F—C₆H₄)₂—CH—(CH₂)₄— | 2-CONH₂ | 1 | 2-Cl | 4-NO₂ | 6-Cl | 2 HCl/0.5 H₂O | 159.0 |
| 29 | 33 | (4-F—C₆H₄)₂—CH—(CH₂)₄— | 2-CONH₂ | 1 | 2-Cl | 4-NH₂ | 6-Cl | 2 HCl/H₂O | 191.4 |
| 30 | 30 | (4-F—C₆H₄)₂—CH—(CH₂)₄— | 2-CONH₂ | 1 | 2-Cl | 4-CN | 6-Cl | base | 102.6 |
| 31 | 37 | (4-F—C₆H₄)₂—CH—(CH₂)₄— | 2-CONH₂ | 1 | 2-Cl | 4-NHCONH₂ | 6-Cl | base | 190.4 |
| 32 | 36 | (4-F—C₆H₄)₂—CH—(CH₂)₄— | 3-CONH₂ | 1 | 2-COCH₃ | 4-NHCOC₂H₅ | H | base | 163.4 |
| 33 | 30 | (4-F—C₆H₄)₂—CH—(CH₂)₄— | 2-CONH₂ | 1 | 2-Cl | 4-Cl | 6-Cl | base | 117.2 |
| 34 | 25 | (4-F—C₆H₄)₂—CH—(CH₂)₄— | 3-CONH₂ | 1 | 2-Cl | 4-CONH₂ | 6-Cl | base | 123.7 |
| 35 | 30 | (4-F—C₆H₄)₂—CH—(CH₂)₄— | 2-CH₃ | 1 | 2-CH₃ | 4-OCH₃ (phenyl) | 6-CH₃ | base | — |
| 36 |  |  | 2-CH₃ |  | 2-CH₃ | 4-OCH₃ | 6-CH₃ |  |  |
| 35 | 35 | (4-F—C₆H₄)₂—CH—(CH₂)₄— | 2-CH₃ | 1 | 2-CH₃ | 4-OH | 6-CH₃ | 2 HCl/0.5 H₂O | 174.2 |

TABLE 1-continued

[Structure: Q—Alk—N(piperidine with X)—N—C$_m$H$_{2m}$—C(O)—NH—C$_6$H$_3$(R$^9$)(R$^{10}$)(R$^{11}$)]

Note: The 4-OCH$_2$—C$_6$H$_5$ group appears as the Q substituent reference structure.

| Comp. No. | Ex. No. | Q—Alk— | X | m | R$^9$ | R$^{10}$ | R$^{11}$ | base/salt | mp. °C. |
|---|---|---|---|---|---|---|---|---|---|
| 37 | 25 | (4-F—C$_6$H$_4$)$_2$—CH—(CH$_2$)$_4$— | 3-CONH$_2$ | 1 | 2-CH$_3$ | 4-OCH$_2$—C$_6$H$_5$ | 6-CH$_3$ | 2 HCl/H$_2$O | 192.8 |
| 38 | 35 | (4-F—C$_6$H$_4$)$_2$—CH—(CH$_2$)$_4$— | 3-CONH$_2$ | 1 | 2-CH$_3$ | 4-OH | 6-CH$_3$ | base | 98.4 |
| 39 | 30 | (4-F—C$_6$H$_4$)$_2$—CH—(CH$_2$)$_4$— | 2-CONH$_2$ | 1 | 2-COCH$_3$ | 4-CONH$_2$ | H | base | 158.5 |
| 40 | 30 | (4-F—C$_6$H$_4$)$_2$—CH—(CH$_2$)$_4$— | 3-CONH$_2$ | 1 | 2-COCH$_3$ | 4-Cl | H | base | 154.1 |
| 41 | 30 | (C$_6$H$_5$)$_2$—CH—(CH$_2$)$_4$— | 2-CONH$_2$ | 1 | 2-CH$_3$ | 6-Cl | H | base | 149.6 |
| 42 | 30 | (4-F—C$_6$H$_4$)$_2$—CH—(CH$_2$)$_4$— | 2-CH$_3$ | 1 | 2-Cl | 4-CONH$_2$ | 6-Cl | 2 HCl/2 H$_2$O | 175.5 |
| 43 | 28 | (4-F—C$_6$H$_4$)$_2$(3-pyridinyl)—CH—(CH$_2$)$_4$— | 3-CONH$_2$ | 1 | 2-Cl | 4-CONH$_2$ | 6-Cl | 3 HCl/3 H$_2$O | 173.0 |
| 44 | 30 | (4-F—C$_6$H$_4$)$_2$—CH—(CH$_2$)$_4$— | 2-CH$_3$ | 1 | 2-C$_2$H$_5$ | 6-C$_2$H$_5$ | H | base | 94.3 |
| 45 | 30 | (4-F—C$_6$H$_4$)$_2$—CH—(CH$_2$)$_4$— | 2-CH$_3$ | 1 | 2-COCH$_3$ | 4-CONH$_2$ | H | 2 HCl/2 H$_2$O | 165.4 |
| 46 | 30 | (3-pyridinyl)(4-F—C$_6$H$_4$)—CH—(CH$_2$)$_4$— | 2-CH$_3$ | 1 | 2-C$_2$H$_5$ | 6-C$_2$H$_5$ | H | 3 HCl/H$_2$O | 168.6 |
| 47 | 30 | (3-pyridinyl)(4-F—C$_6$H$_4$)—CH—(CH$_2$)$_4$— | 2-CH$_3$ | 1 | 2-Cl | 4-COCH$_3$ | 6-Cl | 3 HCl/H$_2$O | 170.7 |
| 48 | 28 | (4-F—C$_6$H$_4$)$_2$—CH—(CH$_2$)$_4$— | 3-CONH$_2$ | 1 | 2-Cl | 4-Cl | 6-Cl | 3 HCl/H$_2$O | 184.4 |
| 49 | 25 | (4-F—C$_6$H$_4$)$_2$—CH—(CH$_2$)$_4$— | 3-CONH$_2$ | 1 | 2-CH$_3$ | 3-COCH$_3$ | 6-CH$_3$ | 2 HCl/0.5 H$_2$O | 191.5 |
| 50 | 25 | (4-F—C$_6$H$_4$)$_2$—CH—(CH$_2$)$_4$— | 3-CONH—CH$_3$ | 1 | 2-Cl | 6-Cl | H | base | 159.8 |
| 51 | 25 | (4-CH$_3$O—C$_6$H$_4$)$_2$—C=CH—(CH$_2$)$_3$— | 3-CONH—CH$_3$ | 1 | 2-Cl | 3-COCH$_3$ | 6-CH$_3$ | 0.5 H$_2$O | 65.1 |
| 52 | 25 | (4-F—C$_6$H$_4$)$_2$—CH—(CH$_2$)$_4$— | 3-CONH—CH$_3$ | 1 | 2-Cl | 6-Cl | H | base | 121.4 |
| 53 | 30 | (4-F—C$_6$H$_4$)$_2$—CH—(CH$_2$)$_4$— | 3-CONH—CH$_3$ | 1 | 2-Cl | 4-COCH$_3$ | 6-Cl | base | 101.5 |
| 54 | 25 | (4-F—C$_6$H$_4$)$_2$—C=CH—(CH$_2$)$_3$— | 2-CH$_3$ | 1 | 2-Cl | 4-CONH$_2$ | 6-Cl | 2 HCl/1.5 H$_2$O/2-propanol | 176.3 |
| 55 | 25 | (4-F—C$_6$H$_4$)$_2$—CH—(CH$_2$)$_4$— | 3-CONH—CH$_3$ | 1 | 2-CH$_3$ | 4-CH$_3$ | H | 2 HCl/0.5 H$_2$O | 190.2 |
| 56 | 25 | (4-F—C$_6$H$_4$)$_2$—C=CH—(CH$_2$)$_3$— | 3-CONH—CH$_3$ | 1 | 2-C$_2$H$_5$ | 6-C$_2$H$_5$ | H | 2 HCl | 204.0 |
| 57 | 25 | (4-F—C$_6$H$_4$)$_2$—CH—(CH$_2$)$_4$— | 3-CONH—CH$_3$ | 1 | 2-C$_2$H$_5$ | 6-C$_2$H$_5$ | H | base | 127.2 |
| 58 | 25 | (4-F—C$_6$H$_4$)$_2$—C=CH—(CH$_2$)$_3$— | 3-CONH—CH$_3$ | 1 | 2-CH$_3$ | 4-CH$_3$ | 6-CH$_3$ | base | 110.3 |
| 59 | 28 | (2-pyridinyl)(4-F—C$_6$H$_4$)—C=CH—(CH$_2$)$_3$— | 3-CONH$_2$ | 1 | 2-Cl | 4-COCH$_3$ | 6-Cl | base | 138.1 |
| 60 | 28 | (3-pyridinyl)(4-F—C$_6$H$_4$)—C=CH—(CH$_2$)$_3$— | 3-CONH—CH$_3$ | 1 | 2-Cl | 6-Cl | H | 3 HCl/3.5 H$_2$O* | 181.3 |
| 61 | 25 | (4-F—C$_6$H$_4$)$_2$—C=CH—(CH$_2$)$_3$— | 3-CONH$_2$ | 1 | 2-Cl | 4-Cl | 6-CH$_3$ | base | 181.6–184.0 |
| 62 | 25 | (4-F—C$_6$H$_4$)$_2$—CH—(CH$_2$)$_4$— | 3-CONH$_2$ | 1 | 2-Cl | 4-Cl | 6-CH$_3$ | base | 165.7–167.5 |
| 63 | 25 | (4-F—C$_6$H$_4$)$_2$—C=CH—(CH$_2$)$_3$— | 3-CONH$_2$ | 1 | 2-C$_2$H$_5$ | 6-C$_2$H$_5$ | H | base | 82.4 |
| 64 | 25 | (4-F—C$_6$H$_4$)$_2$—CH—(CH$_2$)$_4$— | 3-CONH$_2$ | 1 | 2-C$_2$H$_5$ | 6-C$_2$H$_5$ | H | base | 156.8 |
| 65 | 25 | (4-F—C$_6$H$_4$)$_2$—C=CH—(CH$_2$)$_3$— | 3-CONH$_2$ | 1 | 2-Cl | 4-Cl | 6-CH$_3$ | base | 165.0 |
| 66 | 25 | (4-F—C$_6$H$_4$)$_2$—C=CH—(CH$_2$)$_3$— | 3-CONH$_2$ | 1 | 2-CH$_3$ | 4-CH$_3$ | 6-CH$_3$ | base | 130.8 |

TABLE 1-continued structure: Q—Alk—N(piperidine with X substituent)—$C_mH_{2m}$—C(=O)—NH—phenyl(with $R^9$, $R^{10}$, $R^{11}$)

| Comp. No. | Ex. No. | Q—Alk— | X | m | $R^9$ | $R^{10}$ | $R^{11}$ | base/salt | mp. °C. |
|---|---|---|---|---|---|---|---|---|---|
| 67 | 30 | (4-F—$C_6H_4$)$_2$—CH—(CH$_2$)$_4$— | 2-CH$_3$ | 1 | 2-Cl | 4-NO$_2$ | 6-Cl | base | — |
| 68 | 33 | (4-F—$C_6H_4$)$_2$—CH—(CH$_2$)$_4$— | 2-CH$_3$ | 1 | 2-Cl | 4-NH$_2$ | 6-Cl | 3 HCl/1.5 H$_2$O | 172.4 |
| 69 | 30 | (4-F—$C_6H_4$)$_2$—CH—(CH$_2$)$_4$— | 3-CONH$_2$ | 1 | 2-CH$_3$ | 4-OCH$_3$ | 6-CH$_3$ | 2 HCl | 150.4 |
| 70 | 28 | (3-pyridinyl) (4-F—$C_6H_4$)—C=CH—(CH$_2$)$_3$— | 3-CONH$_2$ | 1 | 2-Cl | 6-Cl | H | 3 HCl/2 H$_2$O* | 198.5 |
| 71 | 28 | (3-pyridinyl) (4-F—$C_6H_4$)—C=CH—(CH$_2$)$_3$— | 3-CONH$_2$ | 1 | 2-Cl | 6-Cl | H | base** | 150.5 |
| 72 | 30 | (4-F—$C_6H_4$)$_2$—CH—(CH$_2$)$_4$— | 3-CONH$_2$ | 1 | 2-CH$_3$ | 4-Br | 6-Cl | 2 HCl | 202.6 |
| 73 | 25 | (4-F—$C_6H_4$)$_2$—C=CH—(CH$_2$)$_3$— | 3-CONH—CH$_3$ | 1 | 2-Cl | 4-COCH$_3$ | 6-Cl | base | 82.7 |
| 74 | 25 | (4-F—$C_6H_4$)$_2$—CH—(CH$_2$)$_4$— | 3-CONH—CH$_3$ | 1 | 2-Cl | 4-COCH$_3$ | 6-Cl | base | 87.9 |
| 75 | 30 | (4-F—$C_6H_4$)$_2$—CH—(CH$_2$)$_4$— | 2-CH$_3$ | 1 | 2-Cl | 4-NO$_2$ | H | base | 77.4 |
| 76 | 37 | (4-F—$C_6H_4$)$_2$—CH—(CH$_2$)$_4$— | 3-CH$_3$ | 1 | 2-Cl | 4-NHCONH$_2$ | H | base | 119.9 |
| 77 | 30 | (4-F—$C_6H_4$)$_2$—CH—(CH$_2$)$_4$— | 3-CH$_3$ | 1 | 2-Cl | 6-Cl | H | 2 HCl | 154.1 |
| 78 | 33 | (4-F—$C_6H_4$)$_2$—CH—(CH$_2$)$_4$— | 2-CH$_3$ | 1 | 2-COCH$_3$ | 4-NH$_2$ | H | base | — |
| 79 | 37 | (4-F—$C_6H_4$)$_2$—CH—(CH$_2$)$_4$— | 2-CH$_3$ | 1 | 2-COCH$_3$ | 4-NHCONH$_2$ | H | base | 91.1 |
| 80 | 36 | (4-F—$C_6H_4$)$_2$—CH—(CH$_2$)$_4$— | 2-CH$_3$ | 1 | 2-COCH$_3$ | 4-NHCOC$_2$H$_5$ | H | base | 67.1 |
| 81 | 30 | (4-F—$C_6H_4$)$_2$—CH—(CH$_2$)$_4$— | 3-CONH$_2$ | 1 | 2-Cl | 4-NO$_2$ | 6-Cl | HCl | 155.7 |
| 82 | 36 | (4-F—$C_6H_4$)$_2$—CH—(CH$_2$)$_4$— | 2-CH$_3$ | 1 | 2-COCH$_3$ | 4-NHCOC$_2$H$_5$ | H | base | 95.3 |
| 83 | 34 | (4-F—$C_6H_4$)$_2$—CH—(CH$_2$)$_4$— | 2-CH$_3$ | 1 | 2-Cl | 4-N(CH$_3$)$_2$ | 6-Cl | 2 HCl | 122.0 |
| 84 | 33 | (4-F—$C_6H_4$)$_2$—CH—(CH$_2$)$_4$— | 3-CONH$_2$ | 1 | 2-COCH$_3$ | 4-NH$_2$ | H | 3 HCl | 190.8 |
| 85 | 30 | (4-F—$C_6H_4$)$_2$—CH—(CH$_2$)$_4$— | 2-CH$_3$ | 1 | 2-Cl | 4-NO$_2$ | H | 2 HCl/0.5 H$_2$O | 137.1-140.0 |
| 86 | 30 | (4-F—$C_6H_4$)$_2$—CH—O—(CH$_2$)$_3$— | 2-CH$_3$ | 1 | 2-Cl | 6-Cl | H | base | 123.1 |
| 87 | 30 | (4-F—$C_6H_4$)$_2$—CH(CH$_3$)$_2$— | 2-CH$_3$ | 1 | 2-Cl | 6-Cl | H | 2 HCl/H$_2$O | 135.5 |
| 88 | 25 | (4-F—$C_6H_4$)$_2$—CH—N—(CH$_2$)$_4$— | 3-CONH$_2$ | 1 | 2-Cl | 4-COCH$_3$ | 6-Cl | base | 107.7 |
| 89 | 30 | (3-pyridinyl)—C(=O)— | 2-CH$_3$ | 1 | 2-Cl | 4-COCH$_3$ | 6-Cl | 3 HCl/2 H$_2$O | 189.7 |
| 90 | 30 | (4-F—$C_6H_4$)$_2$—CH—(CH$_2$)$_4$—N—(3-pyridinyl)—(CH$_2$)$_4$— | 2-CH$_3$ | 1 | 2-Cl | 4-COCH$_3$ | 6-Cl | 3 HCl/4 H$_2$O | 200.7 |
| 91 | 30 | (4-F—$C_6H_4$)$_2$—CH—N—(CH$_2$)$_4$— | 3-CONH$_2$ | 1 | 2-Cl | 4-N(CH$_3$)$_2$ | 6-Cl | 3 HCl/1.5 H$_2$O | 201.5 |
| 92 | 30 | (4-F—$C_6H_4$)$_2$—CH—N—(CH$_2$)$_4$— | 2-CH$_3$ | 1 | 2-Cl | 4-N(CH$_3$)$_2$ | 6-Cl | 3 HCl/H$_2$O | 181.6 |
| 93 | 30 | (4-F—$C_6H_4$)$_2$—CH—N—(CH$_2$)$_4$— | 2-CONH$_2$ | 1 | 2-Cl | 4-N(CH$_3$)$_2$ | 6-Cl | base | 190.5 |
| 94 | 30 | (4-F—$C_6H_4$)$_2$—CH—N—(CH$_2$)$_4$— | 2-CONH$_2$ | 1 | 2-Cl | 4-COCH$_3$ | 6-Cl | base | 90.5-93.4 |
| 95 | 30 | (4-F—$C_6H_4$)$_2$—CH—N—(CH$_2$)$_4$— | 2-CH$_3$ | 1 | 2-Cl | 4-NHCH(CH$_3$)$_2$ | 6-Cl | 2 HCl/H$_2$O | 172.6 |
| 96 | 25 | (4-F—$C_6H_4$)$_2$—CH—(3-pyridinyl)—CH—O—(CH$_2$)$_3$— | 2-CH$_3$ | 1 | 2-Cl | 4-COCH$_3$ | 6-Cl | 3 HCl/3 H$_2$O | 170.5 |
| 97 | 27 | (4-F—$C_6H_4$)$_2$—CH—(CH$_2$)$_4$— | 3-CONHCH$_3$ | 1 | 2-Cl | 4-COCH$_3$ | 6-Cl | base | 85-87.1 |
| 98 | 30 | (4-F—$C_6H_4$)$_2$—CH—(CH$_2$)$_4$— | 3-CH$_3$ | 1 | 2-Cl | 4-COCH$_3$ | 6-Cl | 2 HCl/0.5 H$_2$O | 202.9 |
| 99 | 30 | (4-F—$C_6H_4$)$_2$—CH—(CH$_2$)$_4$— | 2-CONH$_2$ | 1 | 2-Cl | 4-COCH$_3$ | 6-Cl | base | 161.8 |
| 100 | 38 | (4-F—$C_6H_4$)$_2$—CH—(CH$_2$)$_4$— | 2-CONH$_2$ | 1 | 2-Cl | 4-CH$_2$NH$_2$ | 6-Cl | base | 160.8 |
| 101 | 25 | (4-F—$C_6H_4$)$_2$—CH—(CH$_2$)$_4$— | 3-CH$_3$ | 1 | 2-Cl | 4-COCH$_3$ | 6-Cl | 2 HCl/H$_2$O | 209.4 |
| 102 | 25 | ($C_6H_5$)$_2$—CH—(CH$_2$)$_4$— | 3-CH$_3$ | 1 | 2-Cl | 4-COCH$_3$ | 6-Cl | 2 HCl | 214-215.4 |
| 103 | 33 | (4-F—$C_6H_4$)$_2$—CH—(CH$_2$)$_4$— | 2-CONH$_2$ | 1 | 2-Cl | 4-NH$_2$ | 6-Cl | base | 213.1 |

TABLE 1-continued
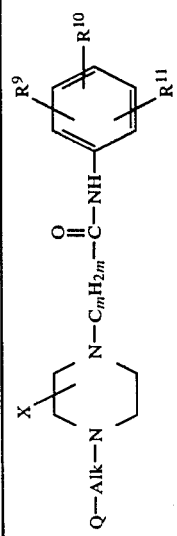
| Comp. No. | Ex. No. | Q—Alk— | X | m | R⁹ | R¹⁰ | R¹¹ | base/salt | mp. °C. |
|---|---|---|---|---|---|---|---|---|---|
| 104 | 25 | (4-CH₃O—C₆H₄)₂—CH—(CH₂)₄— | 3-CONH₂ | 1 | 2-Cl | 4-COCH₃ | 6-Cl | base | 126.3 |
| 105 | 30 | (4-F—C₆H₄)₂—N—C(=O)(CH₂)₃— | 2-CH₃ | 1 | 2-Cl | 6-Cl | H | 2 HCl/H₂O | 223.9 |
| 106 | 30 | (4-F—C₆H₄)₂—N—C(=O)(CH₂)₃— | 2-CONH₂ | 1 | 2-Cl | 6-Cl | H | base | 239.7 |
| 107 | 30 | (4-F—C₆H₄)₂—CH—(CH₂)₄— | 2-CONHCH₃ | 1 | 2-Cl | 4-COCH₃ | 6-Cl | base | 115.1 |
| 108 | 30 | (4-F—C₆H₄)₂—CH—(CH₂)₃— | 3-CONH₂ | 1 | 2-Cl | 6-Cl | H | 2 HCl/H₂O | 182.7 |
| 109 | 28 | (4-F—C₆H₄)₂—CH—(CH₂)₄— | 3-CONH₂ | 1 | 2-Cl | 6-Cl | H | 2 HCl/H₂O | 206.2 |
| 110 | 32 | (4-F—C₆H₄)₂—CH—(CH₂)₄— | 2-CONH₂ | 1 | 2-Cl | 6-Cl | H | 2 HCl | 178.1 |
*Z
**E

TABLE 2

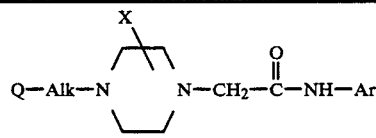

| Comp. No. | Ex. No. | Q—Alk— | X | Ar | base/salt | mp. °C. |
|---|---|---|---|---|---|---|
| 111 | 30 | $(4\text{-}F\text{—}C_6H_4)_2\text{—}CH\text{—}(CH_2)_4\text{—}$ | $2\text{-}CONH_2$ | 2-Cl-3-pyridinyl | HCl/0.5 $H_2O$ | 139.2 |
| 112 | 30 | $(4\text{-}F\text{—}C_6H_4)_2\text{—}CH\text{—}(CH_2)_4\text{—}$ | $2\text{-}CONH_2$ | 2-Cl-6-Cl-3-pyridinyl | HCl | 128.8 |
| 113 | 31 | $(4\text{-}F\text{—}C_6H_4)_2\text{—}CH\text{—}(CH_2)_4\text{—}$ | $2\text{-}CH_3$ | $3\text{-}CH_3\text{-}5\text{-}CH_3\text{-}4\text{-pyridinyl}$ | 3 HCl/$H_2O$ | 159.1 |
| 114 | 31 | $(4\text{-}F\text{—}C_6H_4)_2\text{—}CH\text{—}(CH_2)_4\text{—}$ | $3\text{-}CONH_2$ | $3\text{-}CH_3\text{-}5\text{-}CH_3\text{-}4\text{-pyridinyl}$ | 3 HCl/1.5 $H_2O$ | 238.8 |
| 115 | 31 | $(4\text{-}F\text{—}C_6H_4)_2\text{—}CH\text{—}(CH_2)_4\text{—}$ | $3\text{-}CONH_2$ | $2\text{-}CH_3\text{-}4\text{-}CH_3\text{-}6\text{-}CH_3\text{-}3\text{-pyridinyl}$ | 3 HCl/0.5 $H_2O$ | 224.7 |
| 116 | 31 | $(4\text{-}F\text{—}C_6H_4)_2\text{—}CH\text{—}(CH_2)_4\text{—}$ | $2\text{-}CH_3$ | $2\text{-}CH_3\text{-}4\text{-}CH_3\text{-}6\text{-}CH_3\text{-}3\text{-pyridinyl}$ | base | 135.7 |
| 117 | 31 | $(4\text{-}F\text{—}C_6H_4)_2\text{—}CH\text{—}(CH_2)_4\text{—}$ | $3\text{-}CONH_2$ | $2\text{-}CH_3\text{-}4\text{-}CH_3\text{-}6\text{-}CH_3\text{-}3\text{-pyridinyl}$ | 0.5 $H_2O$ | 100.3 |
| 118 | 31 | $(4\text{-}F\text{—}C_6H_4)_2\text{—}CH\text{—}(CH_2)_4\text{—}$ | $2\text{-}CONH_2$ | $2\text{-}CH_3\text{-}4\text{-}CH_3\text{-}6\text{-}CH_3\text{-}3\text{-pyridinyl}$ | base | 126.8 |
| 119 | 31 | $(4\text{-}F\text{—}C_6H_4)_2\text{—}CH\text{—}(CH_2)_4\text{—}$ | $2\text{-}CONH_2$ | $1\text{-}CH_3\text{-}3\text{-}CH_3\text{-}5\text{-}CH_3\text{-}4\text{-}1\underline{H}\text{-pyrazol}$ | 2 HCl/$H_2O$ | 180.2 |
| 120 | 25 | $(4\text{-}F\text{—}C_6H_4)_2\text{—}CH\text{—}(CH_2)_4\text{—}$ | $3\text{-}CONHCH_3$ | $2\text{-}CH_3\text{-}4\text{-}CH_3\text{-}6\text{-}CH_3\text{-}3\text{-pyridinyl}$ | base | 184.7 |
| 121 | 27 | $(4\text{-}F\text{—}C_6H_4)_2\text{—}N\text{—}(CH_2)_4\text{—}$ | $3\text{-}CONHCH_3$ | $2\text{-}CH_3\text{-}4\text{-}CH_3\text{-}6\text{-}CH_3\text{-}3\text{-pyridinyl}$ | base | 148.0 |
| 122 | 30 | $(4\text{-}F\text{—}C_6H_4)_2\text{—}N\text{—}(CH_2)_4\text{—}$ | $2\text{-}CONH_2$ | $2\text{-}CH_3\text{-}4\text{-}CH_3\text{-}6\text{-}CH_3\text{-}3\text{-pyridinyl}$ | base | 130.0 |
| 123 | 30 | $(4\text{-}F\text{—}C_6H_4)_2\text{—}CH\text{—}(CH_2)_4\text{—}$ | $2\text{-}CONH_2$ | $3\text{-}Br\text{-}5\text{-}CH_3\text{-}4\text{-pyridinyl}$ | base | 119.5 |
| 124 | 30 | $(4\text{-}F\text{—}C_6H_4)_2\text{—}CH\text{—}(CH_2)_4\text{—}$ | $2\text{-}CH_3$ | $3\text{-}Br\text{-}5\text{-}CH_3\text{-}4\text{-pyridinyl}$ | 3 HCl/4.5 $H_2O$ | 196.3 |
| 125 | 30 | $(4\text{-}F\text{—}C_6H_4)_2\text{—}CH\text{—}(CH_2)_4\text{—}$ | $2\text{-}CONH_2$ | 3-Cl-5-Cl-4-pyridinyl | base | 101.8 |

TABLE 3

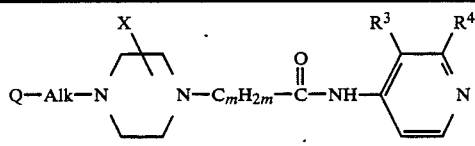

$(CH_2)_s$

| Comp. No. | Ex. No. | Q—Alk— | X | m | $R^3$ | $R^4$ | s | base/salt | mp. °C. |
|---|---|---|---|---|---|---|---|---|---|
| 126 | 31 | $(4\text{-}F\text{—}C_6H_4)_2\text{—}CH\text{—}(CH_2)_4\text{—}$ | $2\text{-}CH_3$ | 1 | $CH_3$ | H | 4 | 3 HCl/$H_2O$ | 204.0 |
| 127 | 30 | $(4\text{-}F\text{—}C_6H_4)_2\text{—}CH\text{—}(CH_2)_4\text{—}$ | $2\text{-}CONH_2$ | 1 | Cl | OH | 3 | base | 176.6 |
| 128 | 30 | $(4\text{-}F\text{—}C_6H_4)_2\text{—}CH\text{—}(CH_2)_4\text{—}$ | $3\text{-}CONH_2$ | 1 | Cl | OH | 3 | base | 140.8 |
| 129 | 25 | $(4\text{-}F\text{—}C_6H_4)_2\text{—}CH\text{—}(CH_2)_4\text{—}$ | $2\text{-}CONHCH_3$ | 1 | Cl | OH | 3 | base | 187.3 |
| 130 | 30 | $(4\text{-}F\text{—}C_6H_4)_2\text{—}CH\text{—}(CH_2)_4\text{—}$ | $3\text{-}CH_3$ | 1 | Cl | OH | 3 | 2 HCl | >300 |
| 131 | 30 | $(4\text{-}F\text{—}C_6H_4)_2\text{—}CH\text{—}(CH_2)_4\text{—}$ | $2\text{-}CH_3$ | 1 | Cl | OH | 3 | 2 HCl/$H_2O$ | 219.4 |
| 132 | 30 | $(4\text{-}F\text{—}C_6H_4)_2\text{—}CH\text{—}(CH_2)_4\text{—}$ | $2\text{-}CH_3$ | 1 | H | OH | 3 | base | 194.4 |
| 133 | 30 | $(4\text{-}F\text{—}C_6H_4)_2\text{—}CH\text{—}(CH_2)_4\text{—}$ | $3\text{-}CH_3$ | 1 | H | OH | 3 | base | 200.8 |
| 134 | 31 | $(4\text{-}F\text{—}C_6H_4)_2\text{—}CH\text{—}(CH_2)_4\text{—}$ | $2\text{-}CONH_2$ | 1 | Br | $CH_3$ | 4 | 2 HCl/2 $H_2O$ | 182.6 |
| 135 | 31 | $(4\text{-}F\text{—}C_6H_4)_2\text{—}CH\text{—}(CH_2)_4\text{—}$ | $2\text{-}CH_3$ | 1 | Br | $CH_3$ | 4 | 3 HCl/2 $H_2O$ | 210.1 |
| 136 | 30 | $(4\text{-}F\text{—}C_6H_4)_2\text{—}CH\text{—}(CH_2)_4\text{—}$ | $2\text{-}CONH_2$ | 1 | Cl | $CH_3$ | 4 | base | 97.7 |
| 137 | 30 | $(4\text{-}F\text{—}C_6H_4)_2\text{—}CH\text{—}(CH_2)_4\text{—}$ | $2\text{-}CONH_2$ | 1 | Br | H | 3 | base | 160.3 |
| 138 | 25 | $(4\text{-}F\text{—}C_6H_4)_2\text{—}CH\text{—}(CH_2)_4\text{—}$ | $2\text{-}CH_3$ | 1 | Br | H | 3 | 3 HCl | 203.5 |
| 139 | 30 | $(4\text{-}F\text{—}C_6H_4)_2\text{—}CH\text{—}(CH_2)_4\text{—}$ | $2\text{-}CONH_2$ | 1 | Br | H | 4 | base | 102.5 |
| 140 | 30 | $(4\text{-}F\text{—}C_6H_4)_2\text{—}CH\text{—}(CH_2)_4\text{—}$ | $2\text{-}CONH_2$ | 1 | Br | H | 5 | base | 145.0 |

(C) Pharmacological Examples

The useful sleep improving properties of the compounds of formula (I) to be used in the method of the present invention can be demonstrated by the following experiment.

Example 39

Slow-wave Sleep in Dogs-Test

Fourteen adult Beagle dogs weighing 15.2±0.79 kg were implanted with cortical and depth electrodes. A minimum period of 4 weeks elapsed between implantation and drug studies. During this time they were adapted to the sound-attenuated and illuminated cage. The dogs' behaviour was followed by closed-circuit television.

Sixteen hours sleep recordings were made from 15.00 to 07.00 h. The first 3 hours were recorded on paper and the whole 16 hours period was analyzed by computer. Visual and computer-analysis was done on 30 sec. epochs, which were classified into wakefulness, transition to sleep, light slow wave sleep, deep slow wave sleep and rapid eye movement (REM) sleep. One cortical derivation (left frontal-occipital), the hippocampus, the electromyogram (EMG) and the electro-oculogram (EOG) were analyzed on-line by a PDP 11/23 computer. Power spectral analysis using a Fast Fourier Transformation was done on the frontal-occipital derivation each 30 sec.

The power in the frequency bands $\delta$ (0.5–3.5 Hz), $\theta$ (3.5–7.5 Hz), $\alpha$ (7.5–13.5 Hz) and $\beta$ (13.5–25 Hz) was calculated. Additionally the power in the $\theta$-band from the hippocampus derivation was calculated, as well as spindly activity. EMG and EOG amplitude. On the basis of these parameters, automatic sleep stage classification was done using a minimal distance approach, Electroencept. clin. Neurophysiol., 46 (1979) 33–48.

The compounds of formula (I) were given orally at the doses 0.16 and 0.63 mg/kg, just preceding the start of the recording. Table 4 illustrates the mean percent difference of slow-wave sleep with the control (equalized at 0%) based on the duration of the stage.

TABLE 4

| Comp. No. | mean percent difference of slow-wave sleep with the control | |
|---|---|---|
| | 0.16 mg/kg | 0.63 mg/kg |
| 108 | 11 | 05 |
| 109 | 12 | 16 |
| 10 | | 19 |
| 11 | | 15 |
| 12 | 20 | 18 |
| 13 | | 17 |
| 14 | 23 | 15 |
| 16 | | 19 |
| 30 | | 14 |
| 31 | | 22 |
| 43 | 23 | |
| 54 | 24 | |
| 86 | 28 | |
| 94 | 20 | |
| 114 | 20 | |
| 115 | 25 | |
| 123 | 25 | |
| 134 | 24 | |

(D) Composition Examples

The following formulations exemplify typical pharmaceutical compositions in dosage unit form suitable for systemic administration to animal and human subjects in accordance with the instant invention. "Active ingredient" (A.I.) as used throughout these examples relates to a compound of formula (I) or a pharmaceutically acceptable acid addition salt thereof.

Example 40: ORAL DROPS

500 Grams of the A.I. was dissolved in 0.5 liters of 2-hydroxypropanoic acid and 1.5 liters of the polyethylene glycol at 60°~80° C. After cooling to 30°~40° C. there were added 35 liters of polyethylene glycol and the mixture was stirred well. Then there was added a solution of 1750 grams of sodium saccharin in 2.5 liters of purified water and while stirring there were added 2.5 liters of cocoa flavor and polyethylene glycol q.s. to a volume of 50 liters, providing an oral drop solution comprising 10 milligrams of the A.I. per milliliter. The resulting solution was filled into suitable containers.

Example 41: ORAL SOLUTION

9 Grams of methyl 4-hydroxybenzoate and 1 gram of propyl 4-hydroxybenzoate were dissolved in 4 liters of boiling purified water. In 3 liters of this solution were dissolved first 10 grams of 2,3-dihydroxybutanedioic acid and thereafter 20 grams of the A.I. The latter solution was combined with the remaining part of the former solution and 12 liters 1,2,3-propanetriol and 3 liters of sorbitol 70% solution were added thereto. 40 Grams of sodium saccharin were dissolved in 0.5 liters of water and 2 milliliters of raspberry and 2 milliliters of gooseberry essence were added. The latter solution was combined with the former, water was added q.s. to a volume of 20 liters providing an oral solution comprising 20 milligrams of the active ingredient per teaspoonful (5 milliliters). The resulting solution was filled in suitable containers.

Example 42: CAPSULES

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelating capsules, comprising each 20 milligrams of the active ingredient.

Example 43: FILM-COATED TABLETS

Preparation of tablet core

A mixture of 100 grams of the A.I., 570 grams lactose and 200 grams starch was mixed well and thereafter humidified with a solution of 5 grams sodium dodecyl sulfate and 10 grams polyvinylpyrrolidone (Kollidon-K 90 ®) in about 200 milliliters of water. The wet powder mixture was sieved, dried and sieved again. Then there was added 100 grams microcrystalline cellulose (Avicel ®) and 15 grams hydrogenated vegetable oil (Sterotex ®). The whole was mixed well and compressed into tablets, giving 10.000 tablets, each containing 10 milligrams of the active ingredient.

Coating

To a solution of 10 grams methyl cellulose (Methocel 60 HG ®) in 75 milliliters of denaturated ethanol there was added a solution of 5 grams of ethyl cellulose (Ethocel 22 cps ®) in 150 milliliters of dichloromethane. Then there were added 75 milliliters of dichloromethane and 2.5 milliliters 1,2,3-propanetriol. 10 Grams of polyethylene glycol was molten and dissolved in 75 milliliters of dichloromethane. The latter solution was added to the former and then there were added 2.5 grams of magnesium octadecanoate, 5 grams of polyvinylpyrrolidone and 30 milliliters of concentrated color suspension (Opaspray K-1-2109 ®) and the whole was homogenated. The tablet cores were coated with the thus obtained mixture in a coating apparatus.

Example 44: INJECTABLE SOLUTION 1.8 Grams methyl 4-hydroxybenzoate and 0.2 grams propyl 4-hydroxybenzoate were dissolved in about 0.5 liters of boiling water for injection. After cooling to about 50° C. there were added while stirring 4 grams lactic acid, 0.05 grams propylene glycol and 4 grams of the A.I.. The solution was cooled to room temperature and supplemented with water for injection q.s. ad 1 liter volume, giving a solution of 4 milligrams A.I. per milliliters. The solution was sterilized by filtration (U.S.P. XVII p. 811) and filled in sterile containers.

Example 45: SUPPOSITORIES

3 Grams A.I. was dissolved in a solution of 3 9rams 2,3-dihydroxybutanedioic acid in 25 milliliters polyethylene glycol 400. 12 Grams surfactant (SPAN ®) and triglycerides (Witepsol 555 ®) q.s. ad 300 grams were molten together. The latter mixture was mixed well with the former solution. The thus obtained mixture was poured into moulds at a temperature of 37°~38° C. to form 100 suppositories each containing 30 milligrams of the active ingredient.

What is claimed is:

1. A compound of the formula:

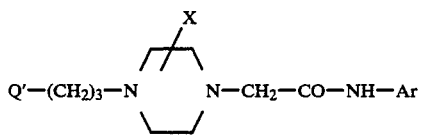

a pharmaceutically acceptable acid addition salt or a stereochemically isomeric form thereof, wherein
X is aminocarbonyl or $C_{1-4}$alkyl;
Ar is 2,6-dihalophenyl substituted in the 4-position with amino, mono- or di($C_{1-4}$alkyl)amino, $C_{1-4}$alkylcarbonylamino, aminocarbonylamino, $C_{1-4}$alkylcarbonyl, aminocarbonyl, cyano, or halo; and
Q' is diarylmethoxy, 2,2-diarylethenyl, or 2,2-diarylethyl; wherein aryl is phenyl, substituted phenyl, or pyridinyl, said substituted phenyl having from 1 to 2 substituents, each independently selected from the group consisting of halo and $C_{1-6}$alkyloxy.

2. A compound according to claim 1 wherein Q is 2,2-di(halophenyl ethenyl or 2,2-di(halophenyl)ethyl.

3. A compound according to claim 1 wherein X is aminocarbonyl.

4. A compound according to claim 1 wherein X is methyl.

5. A compound according to claim 1 wherein the compound is:
3-(aminocarbonyl)-4-[5,5-bis(4-fluorophenyl)-4-pentenyl]-N-(2,6-dichloro-4-cyanophenyl)-1-piperazineacetamide;
3-(aminocarbonyl)-4-[5,5-bis(4-fluorophenyl)pentyl]-N-(2,6-dichloro-4-cyanophenyl)-1-piperazineacetamide;
N-(4-acetyl-2,6-dichlorophenyl)-3-(aminocarbonyl)-4-[5,5-bis(4--fluorophenyl)-4-pentenyl]-1-piperazineacetamide;
N-(4-acetyl-2,6-dichlorophenyl)-3-(aminocaronyl)-4-[5,5-bis(4--fluorophenyl)pentyl]-1-piperazineacetamide; or
3-(aminocarbonyl)-4-[5,5-bis(4-fluorophenyl)pentyl]-N-(2,4,6-trichlorophenyl)-1-piperazineacetamide.

6. A compound according to claim 1 wherein the compound is:
2-(aminocarbonyl)-4-[5,5-bis(4-fluorophenyl)pentyl]-N-(2,6-dichloro-4-cyanophenyl)-1-piperazineacetamide;
2-(aminocarbony1)-N-[4-[(aminocarbonyl)amino]-2,6-dichlorophenyl]-4-[5,5-bis(4-fluorophenyl)pentyl]-1-piperazineacetamide; or
N-(4-acetyl-2,6-dichlorophenyl)-2-(aminocarbonyl)-4-[5,5-bis(4-fluorophenyl)pentyl]-1-piperazineacetamide.

7. A compound according to claim 1 wherein the compound is:
3-(aminocarbonyl)-N-[4-(aminocarbonyl)-2,6-dichlorophenyl]-4-[5-(4-fluorophenyl)-5-(3-pyridinyl)pentyl]-1-piperazineacetamide.

8. A compound according to claim 1 wherein the compound is:
N-(4-acetyl-2,6-dichlorophenyl)-4-[5,5-bis(4-fluorophenyl)pentyl]-2-methyl-1-piperazineacetamide.

9. A sleep improving composition comprising an inert carrier and as active ingredient a sleep-improving amount of a compound of Formula (I') as claimed in claim 1.

10. A composition according to claim 9 wherein the compound is a compound as defined in claim 2.

11. A composition according to claim 9 wherein the compound is a compound as defined in claim 3.

12. A composition according to claim 9 wherein the compound is a compound as defined in claim 4.

13. A composition according to claim 9 wherein the compound is a compound as defined in claim 5.

14. A composition according to claim 9 wherein the compound is a compound as defined in claim 6.

15. A composition according to claim 9 wherein the compound is a compound as defined in claim 7.

16. A composition according to claim 9·wherein the compound is a compound as defined in claim 8.

* * * * *